US011718675B2

(12) United States Patent
Liu et al.

(10) Patent No.: US 11,718,675 B2
(45) Date of Patent: *Aug. 8, 2023

(54) DISRUPTING FC RECEPTOR ENGAGEMENT ON MACROPHAGES ENHANCES EFFICACY OF ANTI-SIRPALPHA ANTIBODY THERAPY

(71) Applicants: The Board of Trustees of the Leland Stanford Junior University, Stanford, CA (US); FORTY SEVEN, INC., Menlo Park, CA (US)

(72) Inventors: Jie Liu, Palo Alto, CA (US); Aaron Michael Ring, New Haven, CT (US); Jens-Peter Volkmer, Menlo Park, CA (US); Irving L. Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 644 days.

This patent is subject to a terminal disclaimer.

(21) Appl. No.: 16/803,751

(22) Filed: Feb. 27, 2020

(65) Prior Publication Data
US 2020/0262918 A1    Aug. 20, 2020

Related U.S. Application Data

(63) Continuation of application No. 15/660,510, filed on Jul. 26, 2017, now Pat. No. 10,611,842.

(60) Provisional application No. 62/370,422, filed on Aug. 3, 2016.

(51) Int. Cl.
*C07K 16/28* (2006.01)
*A61K 39/00* (2006.01)

(52) U.S. Cl.
CPC ........ *C07K 16/283* (2013.01); *A61K 39/0011* (2013.01); *C07K 16/2803* (2013.01); *C07K 16/2827* (2013.01); *C07K 16/2863* (2013.01); *C07K 16/2887* (2013.01); *A61K 2039/507* (2013.01); *A61K 2039/585* (2013.01); *C07K 2317/24* (2013.01); *C07K 2317/52* (2013.01); *C07K 2317/524* (2013.01); *C07K 2317/54* (2013.01); *C07K 2317/71* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,859,739 B2 | 10/2014 | Kontermann et al. | |
| 10,081,680 B2 * | 9/2018 | Weiskopf | A61P 35/00 |
| 2009/0042291 A1 | 2/2009 | Chu et al. | |
| 2014/0242095 A1 | 8/2014 | Wang et al. | |

FOREIGN PATENT DOCUMENTS

| | | | |
|---|---|---|---|
| CN | 103665165 | 3/2014 | |
| JP | 2013-541522 | 11/2013 | |
| JP | 2014-519338 | 8/2014 | |
| WO | 2007/008712 | 1/2007 | |
| WO | 2011/123489 | 10/2011 | |
| WO | WO2012/035141 | 3/2012 | |
| WO | WO2012035141 | 3/2012 | |
| WO | WO2012/172521 | 12/2012 | |
| WO | WO2012172521 | 12/2012 | |
| WO | 2015/138600 A2 | 9/2015 | |
| WO | 2015/138600 A3 | 9/2015 | |
| WO | 2015138600 | 9/2015 | |
| WO | WO2015138600 | 9/2015 | |
| WO | WO-2015138600 A2 * | 9/2015 | ......... A61K 51/1027 |
| WO | WO2017109090 | 6/2017 | |

OTHER PUBLICATIONS

Hwang et al (Methods, 2005, 36:35-42).*
Kurella et al (Bioinformation, 2014, 10:180-186).*
(2001) "Engineered Fc Regions" Review InvivoGen, pp. 1-2.
Leabman et al. (2013) "Effects of altered Fc[gamma]R binding on antibody pharmacokinetics in cynomolgus monkeys", pp. 896-903.
Shields et al. (2001) "High resolution mapping of the binding site on human IgG1 for Fc gamma RI, Fc gamma RII. Fe gamma RIII and FcRn and design of IgG1 variants with improved binding to the Fc gamma R", pp. 6591-6604.
Carter et al. (2006) "Potent Antibody Therapeutics By Design", pp. 343-357.
Review Invivogen (2011), URL https://www.invivogen.com/sites/default/files/invivogen/resources/documents/reviews/review-Engineered-Fc-Regions-invivogen.pdf (describing well-known technique).
Zhao et al., "CD47—signal regulatory protein—α (SIRPα) interactions form a barrier for antibody-mediated tumor cell destruction", Proc Natl Acad Sci, 2011, 108(45): 18342-18347.

(Continued)

*Primary Examiner* — Laura B Goddard
(74) *Attorney, Agent, or Firm* — Pamela J. Sherwood; Bozicevic, Field & Francis LLP

(57) ABSTRACT

Anti-SIRPα antibodies, including multi-specific anti-SIRPα antibodies, are provided, as are related compositions and methods. The antibodies of the disclosure bind to SIRPα and can block the interaction of CD47 on one cell with SIRPα on a phagocytic cell. The subject anti-SIRPα antibodies find use in various therapeutic methods. Embodiments of the disclosure include isolated antibodies and derivatives and fragments thereof, pharmaceutical formulations comprising one or more of the anti-SIRPα antibodies; and cell lines that produce the antibodies. Also provided are amino acid sequences of exemplary anti-SIRPα antibodies.

14 Claims, 6 Drawing Sheets
(6 of 6 Drawing Sheet(s) Filed in Color)
Specification includes a Sequence Listing.

(56) References Cited

OTHER PUBLICATIONS

Gul et al. "Antibody-Dependent Phargocytosis of Tumor Cells by Macrophages: A Potent Effector Mechanism of Monoclonal Antibody Therapy of Cancer", Cancer Research, Dec. 1, 2015, pp. 5008-5013, vol. 75, No. 23, American Association for Cancer Research, Philadelphia, PA.

Leabman, et al., "Effects of Altered Fc-Gamma-R Binding on Antibody Pharmacokinetics in, Cynomolgus Monkeys." mAbs, Nov./Dec. 2013, pp. 896-903, vol. 5, No. 6, Landes Bioscience, Austin, TX.

* cited by examiner

A.

EVQLVQSGAEVKKPGATVKISCKVSGFNIKDYYIHWVQQAPGKGLEWIGRIDPEDGETKYAPK
FQDRATITADTSTDTAYMELSSLRSEDTAVYYCARWGAYWGQGTLVTVSS (SEQ ID NO: 1)

B.

QIVLTQSPPTLSLSPGERVTLTCSASSSVSSSYLYWYQQKPGQAPKLWIYSTNLASGVPARFSG
SGSGTSYTLTISSLQPEDFAVYFCHQWSSYPRTFGAGTKLEIK (SEQ ID NO: 2)

Figure 4

SEQUENCE LISTING

```
<160> NUMBER OF SEQ ID NOS: 10

<210> SEQ ID NO 1
<211> LENGTH: 113
<212> TYPE: PRT
<213> ORGANISM: Artificial Sequence
<220> FEATURE:
<223> OTHER INFORMATION: Humanized antibody

<400> SEQUENCE: 1

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Tyr
            20                  25                  30

Tyr Ile His Trp Val Gln Gln Ala Pro Gly Lys Gly Leu Glu Trp Ile
        35                  40                  45

Gly Arg Ile Asp Pro Glu Asp Gly Glu Thr Lys Tyr Ala Pro Lys Phe
    50                  55                  60

Gln Asp Arg Ala Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Ala Tyr Trp Gly Gln Gly Thr Leu Val Thr Val Ser
            100                 105                 110

Ser

<210> SEQ ID NO 2
<211> LENGTH: 108
<212> TYPE: PRT
<213> ORGANISM: Artificial Sequence
<220> FEATURE:
<223> OTHER INFORMATION: Humanized antibody

<400> SEQUENCE: 2
```

```
Gln Ile Val Leu Thr Gln Ser Pro Pro Thr Leu Ser Leu Ser Pro Gly
1               5                   10                  15

Glu Arg Val Thr Leu Thr Cys Ser Ala Ser Ser Val Ser Ser Ser
            20                  25                  30

Tyr Leu Tyr Trp Tyr Gln Gln Lys Pro Gly Gln Ala Pro Lys Leu Trp
            35                  40                  45

Ile Tyr Ser Thr Ser Asn Leu Ala Ser Gly Val Pro Ala Arg Phe Ser
        50                  55                  60

Gly Ser Gly Ser Gly Thr Ser Tyr Thr Leu Thr Ile Ser Ser Leu Gln
65                  70                  75                  80

Pro Glu Asp Phe Ala Val Tyr Phe Cys His Gln Trp Ser Ser Tyr Pro
                85                  90                  95

Arg Thr Phe Gly Ala Gly Thr Lys Leu Glu Ile Lys
            100                 105
```

<210> SEQ ID NO 3
<211> LENGTH: 5
<212> TYPE: PRT
<213> ORGANISM: Mus musculus

<400> SEQUENCE: 3

```
Asp Tyr Tyr Ile His
1               5
```

<210> SEQ ID NO 4
<211> LENGTH: 17
<212> TYPE: PRT
<213> ORGANISM: Mus musculus

<400> SEQUENCE: 4

```
Arg Ile Asp Pro Glu Asp Gly Glu Thr Lys Tyr Ala Pro Lys Phe Gln
1               5                   10                  15

Asp
```

<210> SEQ ID NO 5
<211> LENGTH: 4
<212> TYPE: PRT
<213> ORGANISM: Mus musculus

<400> SEQUENCE: 5

```
Trp Gly Ala Tyr
1
```

<210> SEQ ID NO 6
<211> LENGTH: 12
<212> TYPE: PRT
<213> ORGANISM: Mus musculus

<400> SEQUENCE: 6

```
Ser Ala Ser Ser Ser Val Ser Ser Ser Tyr Leu Tyr
1               5                   10
```

<210> SEQ ID NO 7
<211> LENGTH: 7
<212> TYPE: PRT
<213> ORGANISM: Mus musculus

<400> SEQUENCE: 7

```
Ser Thr Ser Asn Leu Ala Ser
1               5
```

```
<210> SEQ ID NO 8
<211> LENGTH: 9
<212> TYPE: PRT
<213> ORGANISM: Mus musculus

<400> SEQUENCE: 8

His Gln Trp Ser Ser Tyr Pro Arg Thr
1               5

<210> SEQ ID NO 9
<211> LENGTH: 113
<212> TYPE: PRT
<213> ORGANISM: Mus musculus

<400> SEQUENCE: 9

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
                20                  25                  30

Tyr Ile His Trp Val Gln Arg Thr Glu Gln Gly Leu Glu Trp Ile
            35                  40                  45

Gly Arg Ile Asp Pro Glu Asp Gly Glu Thr Lys Tyr Ala Pro Lys Phe
50                  55                  60

Gln Asp Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Arg Trp Gly Ala Tyr Trp Gly Gln Gly Thr Leu Val Thr Val Ser
            100                 105                 110

Ser

<210> SEQ ID NO 10
<211> LENGTH: 108
<212> TYPE: PRT
<213> ORGANISM: Mus musculus

<400> SEQUENCE: 10

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Ser
                20                  25                  30

Tyr Leu Tyr Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Arg Thr Phe Gly Ala Gly Thr Lys Leu Glu Leu Lys
            100                 105
```

DISRUPTING FC RECEPTOR ENGAGEMENT ON MACROPHAGES ENHANCES EFFICACY OF ANTI-SIRPALPHA ANTIBODY THERAPY

CROSS REFERENCE

This application claims benefit and is a Continuation of application Ser. No. 15/660,510, filed Jul. 26, 2017, which claims benefit of U.S. Provisional Patent Application No. 62/370,422, filed Aug. 3, 2016, which application is incorporated herein by reference in its entirety.

BACKGROUND OF THE INVENTION

Turnover of cells begins with the induction of an apoptotic program or other cellular changes that mark them for removal, and the subsequent recognition of markers by phagocytes, including macrophages, dendritic cells, and the like. This process requires a specific and selective removal of unwanted cells. Unlike healthy cells, the unwanted/aged/dying cells display markers or ligands called "eat-me" signals, i.e. "altered self", which can in turn be recognized by receptors on the phagocytes. Healthy cells may display "don't eat-me" signals that actively inhibit phagocytosis; these signals are either downregulated in the dying cells, are present in an altered conformation or they are superseded by the upregulation of "eat-me" or pro-phagocytic signals. The cell surface protein CD47 on healthy cells and its engagement of a phagocyte receptor, SIRPα, constitutes a key "don't eat-me" signal that can turn off engulfment mediated by multiple modalities, including apoptotic cell clearance and FcR mediated phagocytosis. Blocking the CD47 mediated engagement of SIRPα on a phagocyte can cause removal of live cells bearing "eat me" signals.

CD47 is a broadly expressed transmembrane glycoprotein with a single Ig-like domain and five membrane spanning regions, which functions as a cellular ligand for SIRPα with binding mediated through the NH2-terminal V-like domain of SIRPα. SIRPα is expressed primarily on myeloid cells, including macrophages, granulocytes, myeloid dendritic cells (DCs), mast cells, and their precursors, including hematopoietic stem cells. Structural determinants on SIRPα that mediate CD47 binding are discussed by Lee et al. (2007) J. Immunol. 179:7741-7750; Hatherley et al. (2007) J.B.C. 282:14567-75; and the role of SIRPα cis dimerization in CD47 binding is discussed by Lee et al. (2010) J.B.C. 285:37953-63. In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo.

Programmed cell death (PCD) and phagocytic cell removal are common ways that an organism responds in order to remove damaged, precancerous, or infected cells. Cells that survive this host response (e.g., cancerous cells, chronically infected cells, etc.) have devised ways to evade PCD, and/or phagocytic cell removal. CD47, the "don't eat me" signal, is constitutively upregulated on a wide variety of diseased cells, cancer cells, and infected cells, allowing these cells to evade phagocytosis. Anti-CD47 agents that block the interaction between CD47 on one cell (e.g., a cancer cell, an infected cell, etc.) and SIRPα on another cell (e.g., a phagocytic cell) counteract the increase of CD47 expression and facilitate the phagocytosis of the cancer cell and/or the infected cell. Thus, anti-CD47 agents can be used to treat and/or protect against a wide variety of conditions/disorders. In fact, anti-CD47 and anti-SIRPα blocking antibodies significantly increase phagocytosis of cancer cells in vitro and in vivo. They have been shown to be effective at treating mice engrafted with a wide range of human cancers, from leukemias to solid tumors. However, in some cases an initial high dose of an anti-CD47 agent can cause a dose-dependent loss of red blood cells (RBCs) in mice and non-human primate (NHP) models by binding to CD47 on the surface of the RBCs. The severity of this anemia can preclude the use of higher doses that are required to achieve sustained serum concentrations associated with therapeutic efficacy.

As an alternative to anti-CD47 agents, anti-SIRPα antibodies have potential advantages relating to the relatively restriction expression profile with respect to cell types. Aspects of anti-SIRPα antibodies and the use thereof are provided herein.

SUMMARY

Compositions and methods are provided relating to antibodies that bind to SIRPα and block the interaction between CD47 and SIRPα. Blocking the CD47-SIRPα pathway mediates phagocytosis of targeted cells, and can synergize with other cell targeting agents, including without limitation cancer-specific antibodies; pathogen specific antibodies; and the like. Surprisingly it is shown that activity of an anti-SIRPα antibody on effector cells may be substantially reduced when the antibody productively binds to an Fc receptor on the effector cell surface, including without limitation one or more of FcγRI; FcγRIIA; FcγRIIB1; FcγRIIB2; FcγRIIIA; FcγRIIIB receptors. The reduction in effectiveness can result in inter-individual variation in patient responsiveness. Disabling productive Fc receptor engagement by reducing binding to one or more Fc receptors other than FcRn, where the Fc receptor binds monomeric IgG and/or multimeric immune complexes, can restore activity to the antibody and provide an improved therapeutic profile.

In some embodiments, an antibody is provided comprising (i) a variable region that specifically binds to SIRPα, e.g. human SIRPα, and (ii) an Fc region with reduced binding to Fc receptors, including human Fcγ receptors, relative to a wild-type Fc region; or lacking a functional Fc region. In some embodiments, the antibody specifically binds to human SIRPα. In some embodiments the antibody binds to one or both of human SIRP-β and human SIRPγ. In other embodiments the antibody lacks significant binding to one or both of human SIRP-β and human SIRPγ. In some embodiments the antibody specifically binds to the V1 and V2 isotypes of human SIRPα. In some such embodiments, the Fc region is a human Fc region, where the Fc has been modified by one or more amino acid changes to reduce Fc receptor binding. The antibody may be labeled with a detectable label, immobilized on a solid phase and/or conjugated with a heterologous compound.

The antibody may also be provided as a bispecific or multispecific antibody reactive with a second antigen, particularly including cancer antigens, an immune checkpoint inhibitor, an immune costimulatory agonist, antigens of chronic infection, etc. In some embodiments a bispecific antibody has an active Fc region.

In some embodiments a humanized anti-SIRPα antibody is provided, comprising one or both of a heavy chain variable region as set forth in SEQ ID NO:1; and a light chain variable region sequence set forth in SEQ ID NO:2, or a biologically active variant derived therefrom. In some embodiments the antibody comprises an Fc region, which Fc region is optionally an Fc region with reduced binding to Fc receptors. In other embodiments the antibody lacks an Fc region, e.g. being provided as an F(ab)$_2$ antibody.

The compositions and methods of the invention can be used for the treatment of human disease, where the anti-SIRPα antibody increases phagocytosis of target cells, for example in combination with a second antibody that binds to an antigen on the targeted cell surface. Phagocytic effector cells, including for example macrophages, express a number of Fcγ receptors, and benefit from the use of an anti-SIRPα antibody having decreased FcR binding.

In some embodiments a pharmaceutical formulation is provided, e.g. for use in the treatment of a human subject, where the formulation comprises an antibody comprising (i) a variable region that specifically binds to SIRPα, e.g. human SIRPα, and (ii) an Fc region with reduced binding to Fc receptors, e.g. human Fcγ receptors; or lacking a functional Fc region. In some embodiments, the antibody specifically binds to human SIRPα. In some embodiments the antibody binds to one or both of human SIRP-β and human SIRPγ. In other embodiments the antibody lacks significant binding to one or both of human SIRP-β and human SIRPγ. In some embodiments the antibody specifically binds to the V1 and V2 isotypes of human SIRPα. In some such embodiments, the Fc region is a human Fc region, where the Fc has been modified by one or more amino acid changes to reduce Fc receptor binding. The pharmaceutical formulation may comprise lyophilized antibody; and/or may comprise a pharmaceutically acceptable excipient. The pharmaceutical formulation may be provided as a unit dose, e.g. as a sterile pre-pack in a unit dose with diluent and delivery device, e.g. inhaler, syringe, etc. Pharmaceutical compositions or kits may further comprise a second antibody that binds to a second antigen, e.g., a cancer cell marker, an immune checkpoint inhibitor, an immune costimulatory agonist, a marker of chronic infection, and the like.

The subject antibodies find use in various therapeutic methods, e.g. for the treatment of diseases associated with CD47 in humans, e.g. cancer, chronic infection, atherosclerosis, aneurysm, etc. In some embodiments of method of treatment is provided, comprising contacting an individual with an effective dose of an antibody of the invention, wherein the effective dose provides for binding the antibody of the invention to a phagocytic cell thereby increasing phagocytosis of target cells expressing CD47. Treatment may be systemic or localized, e.g. delivery by intratumoral injection, etc.

The disclosure further provides: isolated nucleic acids encoding the antibodies and variants thereof; a vector comprising that nucleic acid, optionally operably linked to control sequences recognized by a host cell transformed with the vector; a host cell comprising that vector; a process for producing the antibody comprising culturing the host cell so that the nucleic acid is expressed and, optionally, recovering the antibody from the host cell culture (e.g. from the host cell culture medium).

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 4, panels A-B. Amino acid sequence of humanized KWAR (Panel A) heavy chain (SEQ ID NO:1) and (Panel B) light chain (SEQ ID NO:2).

DETAILED DESCRIPTION

Figure 1:
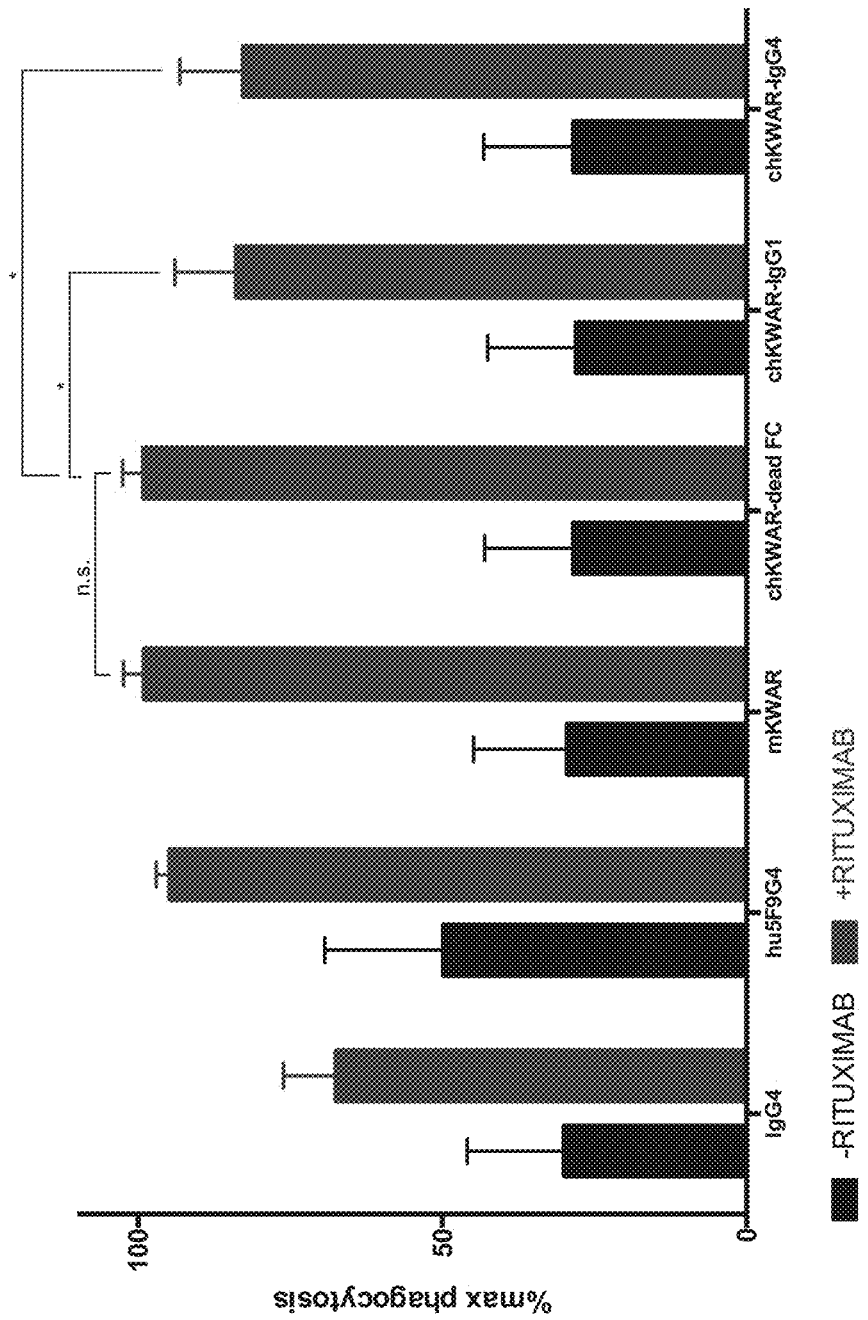
FIG. 1. Combination of anti-CD47 (Hu5F9-G4) or murine anti-SIRPalpha (mKWAR) antibodies with anti-CD20 (Rituximab) antibody enhances the phagocytosis of lymphoma cancer cells (Raji) compared to control IgG4 antibody or monotherapy with Rituximab. Chimeric (mouse antigen binding region, human constant Fc region) antibody variants of KWAR with human IgG1 or human IgG4 lower the phagocytosis enhancing effect compared to a chimeric KWAR antibody with a dead Fc.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer, those with an infection, etc.) as well as those in which prevention is desired (e.g., those with increased susceptibility to cancer, those with an increased likelihood of infection, those suspected of having cancer, those suspected of harboring an infection, etc.).

A therapeutic treatment is one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides). In some embodiments, the affinity of one molecule for another molecule to which it specifically binds is characterized by a $K_d$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_d$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member).

Fc receptors. The human IgG receptor family consists of a number of receptors, including hFcγRI, hFcγRIIA, hFcγRIIC, hFcγRIIIA, hFcγRIIB, hFcγRIIIB. IgG also binds FcRn, which is involved in recycling and transport of IgG. Activation of the Fc receptors may require the FcR subunit to be expressed and functional at the cell surface. Other Fc receptors include, for example, FcαRI (CD89), Fcα/µR, FcεRI, etc. Expression of the Fc receptors varies among immune effector cells. hFcγRI (CD64) is restricted to monocytes/macrophages and dendritic cells (DCs) and, inducibly, expressed on neutrophils and mast cells; hFcγRIIA (CD32A) is expressed on all myeloid cells but not on lymphocytes; hFcγRIIB (CD32B) is highly expressed only on circulating B cells and basophils and expressed on tissue macrophages and DCs, but not on mast cells; hFcγRIIC (CD32C) is expressed on NK cells, monocytes, and neutrophils; hFcγRIIIA (CD16A) is expressed on NK cells and monocytes/macrophages; hFcγRIIIB (CD16B) is expressed on neutrophils and subsets of basophils.

FcRn, which importantly contributes to the biological half-life of antibodies in the blood, is expressed on antigen-presenting cells, monocytes/macrophages, neutrophils, vascular endothelial cells, intestinal epithelial cells, and syncytiotrophoblasts.

The Fcγ receptors differ in their affinity for IgG and likewise the different IgG subclasses have unique affinities for each of the Fcγ receptors. These interactions are further tuned by glycans (oligosaccharide), e.g. at position CH2-

84.4 of IgG. For example, by creating steric hindrance, fucose containing CH2-84.4 glycans reduce IgG affinity for FcγRIIIA.

Fc domain or region. The Fc region of an antibody mediates its serum half-life and effector functions, such as complement-dependent cytotoxicity (CDC), antibody-dependent cellular cytotoxicity (ADCC) and antibody-dependent cell phagocytosis (ADCP). Engineering the Fc region of a therapeutic monoclonal antibody or Fc fusion protein allows the generation of molecules that are better suited to the pharmacology activity required of them. The half-life of an IgG depends on its pH-dependent binding to the neonatal receptor FcRn. FcRn, which is expressed on the surface of endothelial cells, binds the IgG in a pH-dependent manner and protects it from degradation.

A "wild-type Fc region" possesses the effector functions of a native-sequence Fc region, in particular for the purposes of the present invention interacting with one or more of the Fc receptors such as FcγRI; FcγRIIA; FcγRIIB1; FcγRIIB2; FcγRIIIA; FcγRIIIB receptors; and can be assessed using various assays as disclosed, for example, in definitions herein. A "dead" Fc is one that has been mutagenized to retain activity with respect to, for example, prolonging serum half-life through interaction with FcRn, but which has reduced or absent binding to one or more other Fc receptor(s), including without limitation a human FcγR as listed above.

A "native-sequence Fc region" comprises an amino acid sequence identical to the amino acid sequence of an Fc region found in nature. Native-sequence human Fc regions include a native-sequence human IgG1 Fc region (non-A and A allotypes); native-sequence human IgG2 Fc region; native-sequence human IgG3 Fc region; and native-sequence human IgG4 Fc region, as well as naturally occurring variants thereof.

A "variant Fc region" or "engineered Fc region" comprises an amino acid sequence that differs from that of a native-sequence Fc region by virtue of at least one amino acid modification, preferably one or more amino acid substitution(s). Preferably, the variant Fc region has at least one amino acid substitution compared to a native-sequence Fc region or to the Fc region of a parent polypeptide, e.g., from about one to about ten amino acid substitutions, and preferably from about one to about five amino acid substitutions in a native-sequence Fc region or in the Fc region of the parent polypeptide. The variant Fc region herein will preferably possess at least about 80% homology with a native-sequence Fc region and/or with an Fc region of a parent polypeptide, and most preferably at least about 90% homology therewith, more preferably at least about 95% homology therewith.

Variant Fc sequences for a "dead Fc" may include three amino acid substitutions in the CH2 region to reduce FcγRI binding at EU index positions 234, 235, and 237 (see Duncan et al., (1988) Nature 332:563). Two amino acid substitutions in the complement C1q binding site at EU index positions 330 and 331 reduce complement fixation (see Tao et al., J. Exp. Med. 178:661 (1993) and Canfield and Morrison, J. Exp. Med. 173:1483 (1991)). Substitution into human IgG1 of IgG2 residues at positions 233-236 and IgG4 residues at positions 327, 330 and 331 greatly reduces ADCC and CDC (see, for example, Armour K L. et al., 1999 Eur J Immunol. 29(8):2613-24; and Shields R L. et al., 2001. J Biol Chem. 276(9):6591-604).

Binding of IgG to the FcγRs or C1q depends on residues located in the hinge region and the CH2 domain. Two regions of the CH2 domain are critical for FcγRs and C1q binding, and have unique sequences in IgG2 and IgG4. Substitutions into human IgG1 or IgG2 residues at positions 233-236 and IgG4 residues at positions 327, 330 and 331 have been shown to greatly reduce ADCC and CDC. Numerous mutations have been made in the CH2 domain of human IgG1.

The triple amino acid substitution L234A, L235A, and G237A largely eliminates FcγR and complement effector functions (see, for example, US20100266505).

In some embodiments the Fc region has been modified by the choice of expression host, enzymatic treatment of amino acid substitutions to have reduced glycosylation and binding to FcγR, relative to the native protein. Mutations that reduce binding to FcγR include, without limitation, modification of the glycosylation on asparagine 297 of the Fc domain, which is known to be required for optimal FcR interaction. For example known amino acid substitutions include N297 mutations, for example N297A/Q/D/H/G/C, which changes result in the loss of a glycosylation site on the protein. Enzymatically deglycosylated Fc domains, recombinantly expressed antibodies in the presence of a glycosylation inhibitor and the expression of Fc domains in bacteria have a similar loss of glycosylation and consequent binding to FcγRs.

The LALA variant, L234A/L235A, also has significantly reduced FcγR binding; as does E233P/L234V/L235A/G236+A327G/A330S/P331S. See, for example, Armour et al. (1999) Eur J Immunol. 29(8):2613-24. The set of mutations: K322A, L234A and L235A are sufficient to almost completely abolish FcγR and C1q binding. A set of three mutations, L234F/L235E/P331S (dubbed TM), have a very similar effect.

Other Fc variants are possible, including without limitation one in which a region capable of forming a disulfide bond is deleted, or in which certain amino acid residues are eliminated at the N-terminal end of a native Fc form or a methionine residue is added thereto.

The Fc may be in the form of having native sugar chains, increased sugar chains compared to a native form or decreased sugar chains compared to the native form, or may be in an aglycosylated or deglycosylated form. The increase, decrease, removal or other modification of the sugar chains may be achieved by methods common in the art, such as a chemical method, an enzymatic method or by expressing it in a genetically engineered production cell line. Such cell lines can include microorganisms, e.g. Pichia Pastoris, and mammalians cell line, e.g. CHO cells, that naturally express glycosylating enzymes. Further, microorganisms or cells can be engineered to express glycosylating enzymes, or can be rendered unable to express glycosylation enzymes (See e.g., Hamilton, et al., Science, 313:1441 (2006); Kanda, et al, J. Biotechnology, 130:300 (2007); Kitagawa, et al., J. Biol. Chem., 269 (27): 17872 (1994); Ujita-Lee et al., J. Biol. Chem., 264 (23): 13848 (1989); Imai-Nishiya, et al, BMC Biotechnology 7:84 (2007); and WO 07/055916). As one example of a cell engineered to have altered sialylation activity, the alpha-2,6-sialyltransferase 1 gene has been engineered into Chinese Hamster Ovary cells and into sf9 cells. Antibodies expressed by these engineered cells are thus sialylated by the exogenous gene product. A further method for obtaining Fc molecules having a modified amount of sugar residues compared to a plurality of native molecules includes separating said plurality of molecules into glycosylated and non-glycosylated fractions, for example, using lectin affinity chromatography (See e.g., WO 07/117505). The presence of particular glycosylation moieties has been shown to alter the function of Immunoglobulins. For example, the removal of sugar chains from an Fc molecule results in a sharp decrease in binding affinity to the C1q part of the first complement component C1 and a decrease or loss in antibody-dependent cell-mediated cytotoxicity (ADCC) or complement-dependent cytotoxicity (CDC), thereby not inducing unnecessary immune responses in vivo. Additional important modifications include sialylation and fucosylation: the presence of sialic acid in IgG has been correlated with anti-inflammatory activity (See e.g., Kaneko, et al, Science 313:760 (2006)), whereas removal of fucose from the IgG leads to enhanced ADCC activity (See e.g., Shoj-Hosaka, et al, J. Biochem., 140:777 (2006)).

The term "Fc-region-comprising antibody" refers to an antibody that comprises an Fc region. The C-terminal lysine (residue 447 according to the EU numbering system) of the Fc region may be removed, for example, during purification of the antibody or by recombinant engineering the nucleic acid encoding the antibody. Accordingly, an antibody having an Fc region according to this invention can comprise an antibody with or without K447.

Antibodies, also referred to as immunoglobulins, conventionally comprise at least one heavy chain and one light, where the amino terminal domain of the heavy and light chains is variable in sequence, hence is commonly referred to as a variable region domain, or a variable heavy (VH) or variable light (VH) domain. The two domains conventionally associate to form a specific binding region, although as well be discussed here, specific binding can also be obtained with heavy chain only variable sequences, and a variety of non-natural configurations of antibodies are known and used in the art.

A "therapeutic" antibody, as discussed herein, references an antibody that is suitable for treatment of a patient, i.e. an antibody with in vivo activity in a context appropriate for therapeutic use, e.g. treatment of a human subject. In some embodiments, a therapeutic antibody may refer to an antibody that binds to an antigen present on the surface of a targeted cell, e.g. a tumor-specific antigen, a pathogen-specific antigen, etc. Such therapeutic antibodies can be combined with an anti-SIRPα antibody to enhance phagocytosis of the targeted cell.

The term "antibody" herein is used in the broadest sense and specifically covers monoclonal antibodies, polyclonal antibodies, monomers, dimers, multimers, multispecific antibodies (e.g., bispecific antibodies), heavy chain only antibodies, three chain antibodies, single chain Fv, nanobodies, etc., and also include antibody fragments, so long as they exhibit the desired biological activity (Miller et al (2003) Jour. of Immunology 170:4854-4861). For example, F(ab')2 fragments are of interest as a format for anti-SIRPα antibodies. Antibodies may be murine, human, humanized, chimeric, or derived from other species. For many purposes the antibodies of the invention comprise a human engineered Fc region.

The term antibody may reference a full-length heavy chain, a full length light chain, an intact immunoglobulin molecule; or an immunologically active portion of any of these polypeptides. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule, including engineered subclasses with altered Fc portions that provide for reduced effector cell activity. The immunoglobulins can be derived from any species. In one aspect, the immunoglobulin is of largely human origin, is humanized, or chimeric with respect to a human Fc region.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al (1991) Sequences of Proteins of Immunological Interest, 5th Ed. Public Health Service, National Institutes of Health, Bethesda, Md.).

The term "hypervariable region" when used herein refers to the amino acid residues of an antibody which are responsible for antigen-binding. The hypervariable region may comprise amino acid residues from a "complementarity determining region" or "CDR", and/or those residues from a "hypervariable loop". "Framework Region" or "FR" residues are those variable domain residues other than the hypervariable region residues as herein defined.

Variable regions of interest include at least one CDR sequence from the variable regions of an anti-SIRPα antibody, usually at least 2 CDR sequences, and more usually 3 CDR sequences on the light and on the heavy chain. One of skill in the art will understand that a number of definitions of the CDRs are commonly in use, including the Kabat definition (see "Zhao et al. A germline knowledge based computational approach for determining antibody complementarity determining regions." Mol Immunol. 2010; 47:694-700), which is based on sequence variability and is the most commonly used. The Chothia definition is based on the location of the structural loop regions (Chothia et al. "Conformations of immunoglobulin hypervariable regions." Nature. 1989; 342:877-883). Alternative CDR definitions of interest include, without limitation, those disclosed by Honegger, "Yet another numbering scheme for immunoglobulin variable domains: an automatic modeling and analysis tool." J Mol Biol. 2001; 309:657-670; Ofran et al. "Automated identification of complementarity determining regions (CDRs) reveals peculiar characteristics of CDRs and B cell epitopes." J Immunol. 2008; 181:6230-6235; Almagro "Identification of differences in the specificity-determining residues of antibodies that recognize antigens of different size: implications for the rational design of antibody repertoires." J Mol Recognit. 2004; 17:132-143; and Padlan et al. "Identification of specificity-determining residues in antibodies." Faseb J. 1995; 9:133-139., each of which is herein specifically incorporated by reference.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations, which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method.

The antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape, etc.) and human constant region sequences.

An "intact antibody chain" as used herein is one comprising a full length variable region and a full length constant region. An intact "conventional" antibody comprises an intact light chain and an intact heavy chain, as well as a light chain constant domain (CL) and heavy chain constant domains, CH1, hinge, CH2 and CH3 for secreted IgG. Other isotypes, such as IgM or IgA may have different CH domains. The constant domains may be native sequence constant domains (e.g., human native sequence constant domains) or amino acid sequence variants thereof.

"Fv" is the minimum antibody fragment, which contains a complete antigen-recognition and antigen-binding site. The CD3 binding antibodies of the invention comprise a dimer of one heavy chain and one light chain variable domain in tight, non-covalent association; however additional antibodies, e.g. for use in a multi-specific configuration, may comprise a VH in the absence of a VL sequence. Even a single variable domain (or half of an Fv comprising only three hypervariable regions specific for an antigen) has the ability to recognize and bind antigen, although the affinity may be lower than that of two domain binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

"Humanized" forms of non-human (e.g., rodent) antibodies are chimeric antibodies that contain minimal sequence derived from non-human immunoglobulin. See, for example, Jones et al, (1986) Nature 321:522-525; Chothia et al (1989) Nature 342:877; Riechmann et al (1992) J. Mol. Biol. 224, 487-499; Foote and Winter, (1992) J. Mol. Biol. 224:487-499; Presta et al (1993) J. Immunol. 151, 2623-2632; Werther et al (1996) J. Immunol. Methods 157:4986-4995; and Presta et al (2001) Thromb. Haemost. 85:379-389. For further details, see U.S. Pat. Nos. 5,225,539; 6,548,640; 6,982,321; 5,585,089; 5,693,761; 6,407,213; Jones et al (1986) Nature, 321:522-525; and Riechmann et al (1988) Nature 332:323-329.

Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgG, IgE and IgM, bi- or multi-specific antibodies (e.g., Zybodies®, etc), single chain Fvs, polypeptide-Fc fusions, Fabs, cameloid antibodies, masked antibodies (e.g., Probodies®), Small Modular Immuno Pharmaceuticals ("SMIPs™"), single chain or Tandem diabodies (TandAb®), VHHs, Anticalins®, Nanobodies®, minibodies, BiTE®s, ankyrin repeat proteins or DARPINs®, Avimers®, a DART, a TCR-like antibody, Adnectins®, Affilins®, Trans-bodies®, Affibodies®, a TrimerX®, MicroProteins, Fynomers®, Centyrins®, and a KALBITOR®. In some embodiments, an antibody may lack a covalent modification (e.g., attachment of a glycan) that it would have if produced naturally. In some embodiments, an antibody may contain a covalent modification (e.g., attachment of a glycan, a payload, e.g., a detectable moiety, a therapeutic moiety, a catalytic moiety, etc., or other pendant group [e.g., poly-ethylene glycol, etc.

Exemplary antibody agents include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, and antibody fragments. As used herein, the term "antibody agent" also includes intact monoclonal antibodies, polyclonal antibodies, single domain antibodies (e.g., shark single domain antibodies (e.g., IgNAR or fragments thereof)), multispecific antibodies (e.g. bi-specific antibodies) formed from at least two intact antibodies, and antibody fragments so long as they exhibit the desired biological activity. In some embodiments, the term encompasses stapled peptides. In some embodiments, the term encompasses one or more antibody-like binding peptidomimetics. In some embodiments, the term encompasses one or more antibody-like binding scaffold proteins. In come embodiments, the term encompasses monobodies or adnectins.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

Unless specifically indicated to the contrary, the term "conjugate" as described and claimed herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. A conjugate of interest is PEG. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

The anti-SIRPα antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 75% by weight of antibody as determined by the Lowry method, and most preferably more than 80%, 90% or 99% by weight, or (2) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "epitope tagged" when used herein refers to an anti-SIRPα antibody (or fragment) fused to an "epitope tag". The epitope tag polypeptide has enough residues to provide an epitope against which an antibody can be made, yet is short enough such that it does not interfere with activity of the anti-SIRPα antibody. The epitope tag preferably is sufficiently unique so that the antibody specific for the epitope does not substantially cross-react with other epitopes. Suitable tag polypeptides generally have at least 6 amino acid residues and usually between about 8-50 amino acid residues (preferably between about 9-30 residues). Examples include the c-myc tag and the 8F9, 3C7, 6E10, G4, B7 and 9E10 antibodies thereto (Evan et al., Mol. Cell. Biol. 5(12):3610-3616 (1985)); and the Herpes Simplex virus glycoprotein D (gD) tag and its antibody (Paborsky et al., Protein Engineering 3(6):547-553 (1990)). An additional example is a "histidine tag" or "histidine-rich affinity peptide", which is a metal ion affinity peptide that is rich in histidines (e.g., 6xHis tag, HAT tag, 6xHN tag, and the like). A histidine tag can also specifically bind to an anti-His antibody.

SIRPα1 (PTPNS1, SHPS1), is a transmembrane glycoprotein, expressed primarily on myeloid and neuronal cells. SIRPα interacts with the widely distributed membrane protein CD47. In addition to SIRPα, there are two closely related proteins in the SIRP family: SIRPβ and SIRPγ. All three have three immunoglobulin superfamily (IgSF) domains in their extracellular region. In humans, the SIRPα protein is found in two major forms. One form, the variant 1 or V1 form, has the amino acid sequence set out as NCBI RefSeq NP_542970.1 (residues 27-504 constitute the mature form). Another form, the variant 2 or V2 form, differs by 13 amino acids and has the amino acid sequence set out in GenBank as CAA71403.1 (residues 30-504 constitute the mature form). These two forms of SIRPα constitute about 80% of the forms of SIRPα present in humans, and both are embraced herein by the term "human SIRPα". Also embraced by the term "human SIRPα" are the minor forms thereof that are endogenous to humans and have the same property of triggering signal transduction through CD47 upon binding thereto. Sequences of human SIRPα variants may be accessed through public databases, including Genbank accession numbers: ref|NP_542970.1; gb|EAX10606.1; ref|XP_005260726.1; gb|EAX10606.1; XP_005260726.1; gb|EAX10611.1; gb|EAX10609.1; dbj|BAA12974.1; gb|AAH26692.1; ref|XP_011527475.1. See, for example Lee et al. (2007) J. Immunol. 179(11): 7741-7750; herein specifically incorporated by reference.

Antibodies that specifically bind to human SIRPα are known and used in the art, and may be adapted by the use of an engineered Fc region as disclosed herein. Exemplary antibodies include those described in international patent application WO 2015/138600; in published US application 2014/0242095 (University Health Networks); published application CN103665165 (JIANGSU KUANGYA BIOLOGICAL MEDICAL SCIENCE & TECHNOLOGY; Zhao X W et al. *Proc Natl Acad Sci U S A* 108:18342-7 (2011), each herein specifically incorporated by reference. An anti-SIRPα antibody may be pan-specific, i.e. binding to two or more different human SIRPα isoforms; or may be specific for one isoform. For example, the antibody 1.23A described by Zhang et al., supra. is reported to be specific for the SIRPα1 variant, while the 12C4 antibody is pan-specific. Anti-SIRPα antibodies can also be specific for SIRPα and lack binding to SIRPβ and/or SIRPγ. Anti-SIRPa antibodies can be pan-specific with respect to SIRPβ and/or SIRPγ.

The terms "co-administration", "co-administer", and "in combination with" include the administration of two or more therapeutic agents either simultaneously, concurrently or sequentially within no specific time limits. In one embodiment, the agents are present in the cell or in the subjects body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

Anti-SIRPα antibodies may be used therapeutically in combination with a second antibody or agent that selectively binds to a target cell. The term "target cell" can be used in different ways depending on context. Typically a "target cell" is a cell that will be phagocytosed by a phagocytic cell (e.g., a phagocyte), where the phagocytosis is enhanced as a result of administering a subject anti-SIRPα antibody. Thus, the term "target cell" can refer to a CD47-expressing cell, because a subject anti-SIRPα antibody, by inhibiting the interaction between the CD47-expressing cell and the SIRPα expressing phagocytic cell, facilitates phagocytosis of the CD47-expressing cell.

However, in some cases, the target cell need not express high levels of CD47 (and in some cases need not express CD47 at all) in order for a subject multispecific antibody to induce phagocytosis of the target cell. For example, in the context of a multispecific (e.g., bispecific) antibody, the SIRPα binding region (the first binding region) of a subject multispecific (e.g., bispecific) antibody binds to SIRPα on a phagocytic cell (e.g., a macrophage), which allows the multispecific antibody to function as a tether to bring the phagocytic cell into the vicinity of a cell expressing an antigen (e.g., a marker of a cancer cell) that is recognized by (specifically bound by) a second binding region of the multispecific antibody (e.g., the second binding region of a bispecific antibody). Therefore, in the context of a multispecific antibody, a target cell can be a cell that does not express high levels of CD47 (and can also be a cell that does not express CD47). In some embodiments, a target cell is a mammalian cell, for example a human cell. A target cell can be from any individual (e.g., patient, subject, and the like) as described below.

In some cases, a target cell is an "inflicted" cell (e.g., a cell from an "inflicted" individual), where the term "inflicted" is used herein to refer to a subject with symptoms, an illness, or a disease that can be treated with a subject anti-SIRPα antibody. An "inflicted" subject can have cancer, can harbor an infection (e.g., a chronic infection), and/or can have other hyper-proliferative conditions, for example sclerosis, fibrosis, and the like, etc. Also of interest is the use in the treatment of cardiovascular conditions, including without limitation aneurysm, atherosclerosis, etc. "Inflicted cells" can be those cells that cause the symptoms, illness, or disease. As non-limiting examples, the inflicted cells of an inflicted patient can be CD47 expressing cancer cells, infected cells, inflammatory cells, immune cells, and the like. One indication that an illness or disease can be treated with a subject anti-SIRPα antibody is that the involved cells (i.e., the inflicted cells, e.g., the cancerous cells, the infected cells, the inflammatory cells, the immune cells, etc.) express CD47 (e.g., in some cases, an increased level of CD47 compared to normal cells of the same cell type).

For the treatment of cancer, the anti-SIRPα antibody may be combined with one or more antibodies specific for a tumor antigen. Of these, tumor-associated antigens (TAAs) are relatively restricted to tumor cells, whereas tumor-specific antigens (TSAs) are unique to tumor cells. TSAs and TAAs typically are portions of intracellular molecules expressed on the cell surface as part of the major histocompatibility complex.

Tissue specific differentiation antigens are molecules present on tumor cells and their normal cell counterparts. Tumor-associated antigens known to be recognized by therapeutic mAbs fall into several different categories. Hematopoietic differentiation antigens are glycoproteins that are usually associated with cluster of differentiation (CD) groupings and include CD20, CD30, CD33 and CD52. Cell surface differentiation antigens are a diverse group of glycoproteins and carbohydrates that are found on the surface of both normal and tumor cells. Antigens that are involved in growth and differentiation signaling are often growth factors and growth factor receptors. Growth factors that are targets for antibodies in cancer patients include CEA, epidermal growth factor receptor (EGFR; also known as ERBB1)' ERBB2 (also known as HER2), ERBB3, MET (also known as HGFR), insulin-like growth factor 1 receptor (IGF1 R), ephrin receptor A3 (EPHA3), tumor necrosis factor (TNF)-related apoptosis-inducing ligand receptor 1 (TRAILR1; also known as TNFRSF10A), TRAILR2 (also known as TNFRSF10B) and receptor activator of nuclear factor-κB ligand (RANKL; also known as TNFSF11). Antigens involved in angiogenesis are usually proteins or growth factors that support the formation of new microvasculature, including vascular endothelial growth factor (VEGF), VEGF receptor (VEGFR), integrin αVβ3 and integrin α5β1. Tumor stroma and the extracellular matrix are indispensable support structures for a tumor. Stromal and extracellular matrix antigens that are therapeutic targets include fibroblast activation protein (FAP) and tenascin.

Examples of therapeutic antibodies useful in bispecific configurations or as combination therapy include, without limitation, rituximab; Ibritumomab; tiuxetan; tositumomab; Brentuximab; vedotin; Gemtuzumab; ozogamicin; Alemtuzumab; IGN101; adecatumumab; Labetuzumab; huA33; Pemtumomab; oregovomab; CC49 (minretumomab); cG250; J591; MOv18; MORAb-003 (farletuzumab); 3F8, ch14.18; KW-2871; hu3S193; IgN311; Bevacizumab; IM-2C6; CDP791; Etaracizumab; Volociximab; Cetuximab, panitumumab, nimotuzumab; 806; Trastuzumab; pertuzumab; MM-121; AMG 102, METMAB; SCH 900105; AVE1642, IMC-A12, MK-0646, R1507; CP 751871; KB004; IIIA4; Mapatumumab (HGS-ETR1); HGS-ETR2; CS-1008; Denosumab; Sibrotuzumab; F19; and 81C6. A bispecific antibody may use the Fc region that activates an Fcγ receptor.

For the treatment of cancer, the anti-SIRPα antibody may be combined with one or more antibodies that inhibit immune checkpoint proteins. Of particular interest are immune checkpoint proteins displayed on the surface of a tumor cell. The immune-checkpoint receptors that have been most actively studied in the context of clinical cancer immunotherapy, cytotoxic T-lymphocyte-associated antigen 4 (CTLA4; also known as CD152) and programmed cell death protein 1 (PD1; also known as CD279)—are both inhibitory receptors. The clinical activity of antibodies that block either of these receptors implies that antitumor immunity can be enhanced at multiple levels and that combinatorial strategies can be intelligently designed, guided by mechanistic considerations and preclinical models.

The two ligands for PD1 are PD1 ligand 1 (PDL1; also known as B7-H1 and CD274) and PDL2 (also known as B7-DC and CD273). PDL1 is expressed on cancer cells and through binding to its receptor PD1 on T cells it inhibits T cell activation/function. See, for example, Avelumab as a therapeutic antibody.

Agents that agonize an immune costimulatory molecule are also useful in the methods of the invention. Such agents include agonists or CD40 and OX40. CD40 is a costimulatory protein found on antigen presenting cells (APCs) and is required for their activation. These APCs include phagocytes (macrophages and dendritic cells) and B cells. CD40 is part of the TNF receptor family. The primary activating signaling molecules for CD40 are IFNγ and CD40 ligand (CD40L). Stimulation through CD40 activates macrophages.

Anti CCR4 (CD194) antibodies of interest include humanized monoclonal antibodies directed against C-C chemokine receptor 4 (CCR4) with potential anti-inflammatory and antineoplastic activities.

Examples of symptoms, illnesses, and/or diseases that can be treated with a subject anti-SIRPα antibody include, but are not limited to cancer (any form of cancer, including but not limited to: carcinomas, soft tissue tumors, sarcomas, teratomas, melanomas, leukemias, lymphomas, brain cancers, solid tumors, mesothelioma (MSTO), etc.); infection (e.g., chronic infection); and an immunological disease or disorder (e.g., an inflammatory disease)(e.g., multiple sclerosis, arthritis, and the like, e.g., for immunosuppressive therapy). A subject anti-SIRPα antibody can also be used for transplant conditioning (e.g., stem cell transplant, bone marrow transplant, etc.) (e.g., to destroy malignant cells, to provide immunosuppression to prevent the patient's body from rejecting the donor's cells/stem cells, etc.). For example, in some cases, a subject antibody combination or bispecific antibody (e.g., anti-SIRPα in combination with anti-CD117) finds use for transplant conditioning. For example, a subject antibody combination or bispecific antibody (e.g., anti-SIRPα in combination with anti-CD117) can be used for bone marrow transplant conditioning. In some cases, a subject anti-SIRPα antibody (e.g., an antibody combination) can be used for immunosuppressive therapy.

For example, any cancer, where the cancer cells exhibit increased expression of CD47 compared to non-cancer cells, is a suitable cancer to be treated by the subject methods and compositions. As used herein "cancer" includes any form of cancer, including but not limited to solid tumor cancers (e.g., lung, prostate, breast, bladder, colon, ovarian, pancreas, kidney, liver, glioblastoma, medulloblastoma, leiomyosarcoma, head & neck squamous cell carcinomas, melanomas, neuroendocrine; etc.) and liquid cancers (e.g., hematological cancers); carcinomas; soft tissue tumors; sarcomas; teratomas; melanomas; leukemias; lymphomas; and brain cancers, including minimal residual disease, and including both primary and metastatic tumors. Any cancer, where the cancer cells express CD47 (e.g., in some cases, the cancer cells exhibit increased expression of CD47 compared to non-cancer cells), is a suitable cancer to be treated by the subject methods and compositions (e.g., a subject anti-SIRPα antibody).

Carcinomas are malignancies that originate in the epithelial tissues. Epithelial cells cover the external surface of the body, line the internal cavities, and form the lining of glandular tissues. Examples of carcinomas include, but are not limited to: adenocarcinoma (cancer that begins in glandular (secretory) cells), e.g., cancers of the breast, pancreas, lung, prostate, and colon can be adenocarcinomas; adrenocortical carcinoma; hepatocellular carcinoma; renal cell carcinoma; ovarian carcinoma; carcinoma in situ; ductal carcinoma; carcinoma of the breast; basal cell carcinoma; squamous cell carcinoma; transitional cell carcinoma; colon carcinoma; nasopharyngeal carcinoma; multilocular cystic renal cell carcinoma; oat cell carcinoma; large cell lung carcinoma; small cell lung carcinoma; non-small cell lung carcinoma; and the like. Carcinomas may be found in prostrate, pancreas, colon, brain (usually as secondary metastases), lung, breast, skin, etc.

Soft tissue tumors are a highly diverse group of rare tumors that are derived from connective tissue. Examples of soft tissue tumors include, but are not limited to: alveolar soft part sarcoma; angiomatoid fibrous histiocytoma; chondromyxoid fibroma; skeletal chondrosarcoma; extraskeletal myxoid chondrosarcoma; clear cell sarcoma; desmoplastic small round-cell tumor; dermatofibrosarcoma protuberans; endometrial stromal tumor; Ewing's sarcoma; fibromatosis (Desmoid); fibrosarcoma, infantile; gastrointestinal stromal tumor; bone giant cell tumor; tenosynovial giant cell tumor; inflammatory myofibroblastic tumor; uterine leiomyoma; leiomyosarcoma; lipoblastoma; typical lipoma; spindle cell or pleomorphic lipoma; atypical lipoma; chondroid lipoma; well-differentiated liposarcoma; myxoid/round cell liposarcoma; pleomorphic liposarcoma; myxoid malignant fibrous histiocytoma; high-grade malignant fibrous histiocytoma; myxofibrosarcoma; malignant peripheral nerve sheath tumor; mesothelioma; neuroblastoma; osteochondroma; osteosarcoma; primitive neuroectodermal tumor; alveolar rhabdomyosarcoma; embryonal rhabdomyosarcoma; benign or malignant schwannoma; synovial sarcoma; Evan's tumor; nodular fasciitis; desmoid-type fibromatosis; solitary fibrous tumor; dermatofibrosarcoma protuberans (DFSP); angiosarcoma; epithelioid hemangioendothelioma; tenosynovial giant cell tumor (TGCT); pigmented villonodular synovitis (PVNS); fibrous dysplasia; myxofibrosarcoma; fibrosarcoma; synovial sarcoma; malignant peripheral nerve sheath tumor; neurofibroma; and pleomorphic adenoma of soft tissue; and neoplasias derived from fibroblasts, myofibroblasts, histiocytes, vascular cells/endothelial cells and nerve sheath cells.

A sarcoma is a rare type of cancer that arises in cells of mesenchymal origin, e.g., in bone or in the soft tissues of the body, including cartilage, fat, muscle, blood vessels, fibrous tissue, or other connective or supportive tissue. Different types of sarcoma are based on where the cancer forms. For example, osteosarcoma forms in bone, liposarcoma forms in fat, and rhabdomyosarcoma forms in muscle. Examples of sarcomas include, but are not limited to: askin's tumor; sarcoma botryoides; chondrosarcoma; ewing's sarcoma; malignant hemangioendothelioma; malignant schwannoma; osteosarcoma; and soft tissue sarcomas (e.g., alveolar soft part sarcoma; angiosarcoma; cystosarcoma phyllodesdermatofibrosarcoma protuberans (DFSP); desmoid tumor; desmoplastic small round cell tumor; epithelioid sarcoma; extraskeletal chondrosarcoma; extraskeletal osteosarcoma; fibrosarcoma; gastrointestinal stromal tumor (GIST); hemangiopericytoma; hemangiosarcoma (more commonly referred to as "angiosarcoma"); kaposi's sarcoma; leiomyosarcoma; liposarcoma; lymphangiosarcoma; malignant peripheral nerve sheath tumor (MPNST); neurofibrosarcoma; synovial sarcoma; undifferentiated pleomorphic sarcoma, and the like).

A teratomas is a type of germ cell tumor that may contain several different types of tissue (e.g., can include tissues derived from any and/or all of the three germ layers: endoderm, mesoderm, and ectoderm), including for example, hair, muscle, and bone. Teratomas occur most often in the ovaries in women, the testicles in men, and the tailbone in children.

Melanoma is a form of cancer that begins in melanocytes (cells that make the pigment melanin). It may begin in a mole (skin melanoma), but can also begin in other pigmented tissues, such as in the eye or in the intestines.

Leukemias are cancers that start in blood-forming tissue, such as the bone marrow, and causes large numbers of abnormal blood cells to be produced and enter the bloodstream. For example, leukemias can originate in bone marrow-derived cells that normally mature in the bloodstream. Leukemias are named for how quickly the disease develops and progresses (e.g., acute versus chronic) and for the type of white blood cell that is effected (e.g., myeloid versus lymphoid). Myeloid leukemias are also called myelogenous or myeloblastic leukemias. Lymphoid leukemias are also called lymphoblastic or lymphocytic leukemia. Lymphoid leukemia cells may collect in the lymph nodes, which can become swollen. Examples of leukemias include, but are not limited to: Acute myeloid leukemia (AML), Acute lymphoblastic leukemia (ALL), Chronic myeloid leukemia (CML), and Chronic lymphocytic leukemia (CLL).

Lymphomas are cancers that begin in cells of the immune system. For example, lymphomas can originate in bone marrow-derived cells that normally mature in the lymphatic system. There are two basic categories of lymphomas. One kind is Hodgkin lymphoma (HL), which is marked by the presence of a type of cell called the Reed-Sternberg cell. There are currently 6 recognized types of HL. Examples of Hodgkin lymphomas include: nodular sclerosis classical Hodgkin lymphoma (CHL), mixed cellularity CHL, lymphocyte-depletion CHL, lymphocyte-rich CHL, and nodular lymphocyte predominant HL.

The other category of lymphoma is non-Hodgkin lymphomas (NHL), which includes a large, diverse group of cancers of immune system cells. Non-Hodgkin lymphomas can be further divided into cancers that have an indolent (slow-growing) course and those that have an aggressive (fast-growing) course. There are currently 61 recognized types of NHL. Examples of non-Hodgkin lymphomas include, but are not limited to: AIDS-related Lymphomas, anaplastic large-cell lymphoma, angioimmunoblastic lymphoma, blastic NK-cell lymphoma, Burkitt's lymphoma, Burkitt-like lymphoma (small non-cleaved cell lymphoma), chronic lymphocytic leukemia/small lymphocytic lymphoma, cutaneous T-Cell lymphoma, diffuse large B-Cell lymphoma, enteropathy-type T-Cell lymphoma, follicular lymphoma, hepatosplenic gamma-delta T-Cell lymphomas, T-Cell leukemias, lymphoblastic lymphoma, mantle cell lymphoma, marginal zone lymphoma, nasal T-Cell lymphoma, pediatric lymphoma, peripheral T-Cell lymphomas, primary central nervous system lymphoma, transformed lymphomas, treatment-related T-Cell lymphomas, and Waldenstrom's macroglobulinemia.

Brain cancers include any cancer of the brain tissues. Examples of brain cancers include, but are not limited to: gliomas (e.g., glioblastomas, astrocytomas, oligodendrogliomas, ependymomas, and the like), meningiomas, pituitary adenomas, vestibular schwannomas, primitive neuroectodermal tumors (medulloblastomas), etc.

As used herein, the term "infection" refers to any state in at least one cell of an organism (i.e., a subject) is infected by an infectious agent (e.g., a subject has an intracellular pathogen infection, e.g., a chronic intracellular pathogen infection). As used herein, the term "infectious agent" refers to a foreign biological entity (i.e. a pathogen) that induces CD47 expression (e.g., increased CD47 expression) in at least one cell of the infected organism. For example, infectious agents include, but are not limited to bacteria, viruses, protozoans, and fungi. Intracellular pathogens are of particular interest. Infectious diseases are disorders caused by infectious agents. Some infectious agents cause no recognizable symptoms or disease under certain conditions, but have the potential to cause symptoms or disease under changed conditions. The subject methods can be used in the treatment of chronic pathogen infections, for example including but not limited to viral infections, e.g. retrovirus, lentivirus, hepadna virus, herpes viruses, pox viruses, human papilloma viruses, etc.; intracellular bacterial infections, e.g. *Mycobacterium, Chlamydophila, Ehrlichia, Rickettsia, Brucella, Legionella, Francisella, Listeria, Coxiella, Neisseria, Salmonella, Yersinia* sp, *Helicobacter pylori* etc.; and intracellular protozoan pathogens, e.g. *Plasmodium* sp, *Trypanosoma* sp., *Giardia* sp., *Toxoplasma* sp., *Leishmania* sp., etc.

Also of interest for treatment with anti-SIRPα antibodies is the prevention and treatment of coronary artery disease (CAD) in a subject, including without limitation methods of preventing or treating atherosclerosis, aneurysm, etc., for example as described in patent publications WO 2015/041987; WO 2016/138306; WO 2016/044021, each herein specifically incorporated by reference.

Polypeptides

In one aspect, the present disclosure is directed to antibodies (and cell lines that produce such antibodies) that specifically bind human SIRPα (i.e., an anti-SIRPα antibody) and reduce the interaction between CD47 on one cell (e.g., a cancerous cell, an infected cell, etc.) and SIRPα on another cell (e.g., a phagocytic cell). The antibody comprises (i) a variable region that specifically binds to SIRPα, e.g. human SIRPα, and (ii) an Fc region with reduced binding to one or more Fc receptors other than FcRn, including human Fcγ receptors; or lacks an Fc region. In such embodiments, the Fc region is a human Fc region, where the Fc has been modified, or engineered, by one or more amino acid changes to reduce Fc receptor binding. Specific anti-SIRPα antibodies include, without limitation, KWAR23, which antibody is disclosed herein in a chimeric and humanized format.

The antibody may also be provided as a bispecific or multispecific antibody reactive with a second antigen, particularly including cancer antigens, an immune checkpoint inhibitor, an immune costimulatory agonist, antigens of chronic infection, etc. Anti-SIRPα antibodies can bind SIRPα without inhibiting phagocytosis (activating or stimulating signaling through SIRPα inhibits phagocytosis). In other words, anti-SIRPα antibodies may bind SIRPα, but block CD47-induced SIRPα signaling. Thus, suitable anti-SIRPα antibodies facilitate the preferential phagocytosis of inflicted cells (e.g., cancerous cells, infected cells, etc.) over normal cells by inhibiting CD47-induced SIRPα signaling, with reduced binding to an FcR present on effector cells, particularly present on human macrophages.

Data provided herein indicate that activity e.g. in enhancing phagocytosis when combined with a cell-targeted antibody, of an anti-SIRPα antibody comprising an wild-type human Fc region such as an IgG4 or IgG1 region can show inter-individual variability. In particular, some individuals (responders) respond by a synergistic increase in phagocytosis, while other individuals (non-responders) lack a significant enhancement of phagocytosis. The number of non-responders in a population will vary with the composition of the population, but may be up to about 10%, up to about 20%, up to about 30%, up to about 40%, up to about 50%, up to about 60%, up to about 70%, up to about 80%, up to about 90% or more. For clinical purposes it is undesirable to have non-responders in the population. Use of an anti-SIRPα antibody that comprises a "dead" Fc, i.e. a human Fc sequence engineered to have reduced binding to one or more human FcR other than FcRn, reduces the number of non-responders in a population, e.g. reducing the number of non-responders by up to about 10%, up to about 20%, up to about 30%, up to about 40%, up to about 50%, up to about 60%, up to about 70%, up to about 80%, up to about 90% or more.

As used herein, the term "non-responder" refers to an individual for which the addition of an anti-SIRPα antibody to a therapy comprising administration of a cell-targeting antibody does not significantly enhance the effectiveness of the cell-targeting antibody. A "responder" is an individual for which the addition of an anti-SIRPα antibody to a therapy comprising administration of a cell-targeting antibody significantly enhances the effectiveness of the cell-targeting antibody, and may provide for a synergistic response, in which the level of activity is greater than the activity of either antibody as a monotherapy, e.g. when normalized to a negative control.

Suitable anti-SIRPα antibodies include fully human, humanized or chimeric versions of such antibodies, where the Fc region is modified by one or more amino acid changes to reduce FcR binding to one or more Fc other than FcRn. Humanized antibodies are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Variable regions of exemplary antibodies are provided. In some embodiments the variable region comprises the CDR sequences of KWAR23, e.g. as set forth in SEQ ID NO:3, 4, 5 for the heavy chain; and 6, 7, 8 for the light chain, joined to a "dead" Fc region or lacking an Fc region. Antibodies of interest include these provided combinations, as well as fusions of the variable regions to appropriate constant regions or fragments of constant regions, e.g. to generate F(ab)' antibodies. Variable regions of interest include at least one CDR sequence of the provided anti-SIRPα antibody, where a CDR may be 3, 4, 5, 6, 7, 8, 9, 10, 11, 12 or more amino acids. Alternatively, antibodies of interest include a variable region as set forth in the provided antibodies, or pairs of variable regions sequences as set forth herein.

In other embodiments, a humanized KWAR23 antibody is provided, which antibody comprises one or both of the variable region sequences provided in SEQ ID NO:1 and SEQ ID NI:2, or a biologically active variant derived therefrom. Humanized KWAR23 may comprise a wild-type Fc region, e.g. a human Fc region; or may comprise a modified Fc region, e.g. a dead Fc.

Biologically active variants of humanized KWAR23 can include an amino acid sequence that is 80% or more, 85% or more, 90% or more, 92% or more, 95% or more, 97% or more, 98% or more, 99% or more, 99.5% or more, or 100% identical to an amino acid sequence set forth in SEQ ID NO:1 or SEQ ID NO:2. In some embodiments the amino acid sequence comprises not more than 1, not more than 2, not more than 3, not more than 4, not more than 5, not more than 6, not more than 7, not more than 8, not more than 9, not more than 10, etc. amino acid changes relative to the sequence of SEQ ID NO:1 or SEQ ID NO:2. In some embodiments, amino acid changes are in residues other than CDR residues, as defined, for example, in SEQ ID NO:3, 4, 5, 6, 7, 8, i.e. amino acid changes are in framework sequences. A biologically active variant retains the ability to specifically bind to human SIRPα, usually both the V1 and the V2 variant.

In some embodiments a subject anti-SIRPα antibody includes one more CDRs (e.g., 2 or more, 3 or more, 4 or more, 5 or more, or 6 CDRs) that includes an amino acid sequence set forth in SEQ ID NOs: 3-5 and 6-8. A subject anti-SIRPα antibody can include a CDR sequence that differs by up to 6 amino acids (e.g., up to 5 amino acids, up to 4 amino acids, up to 3 amino acids, up to 2 amino acids, or up to 1 amino acid) as compared to a CDR amino acid sequence set forth in any of SEQ ID NOs: 3-5 and 6-8.

In some cases, a subject anti-SIRPα antibody includes one or more CDRs (e.g., 2 or more, 3 or more, 4 or more, 5 or more, 6, or 6 or more) having an amino acid sequence that differs by up to 6 amino acids (e.g., up to 5 amino acids, up to 4 amino acids, up to 3 amino acids, up to 2 amino acids, or up to 1 amino acid) as compared to a CDR amino acid sequence set forth in any of SEQ ID NOs: 3-5 and 6-8. In some cases, a subject anti-SIRPα antibody includes two or more CDRs (e.g., 3 or more, 4 or more, 5 or more, 6, or 6 or more) that have an amino acid sequence that differs by up to 6 amino acids (e.g., up to 5 amino acids, up to 4 amino acids, up to 3 amino acids, up to 2 amino acids, or up to 1 amino acid) as compared to a CDR amino acid sequence set forth in any of SEQ ID NOs: 3-5 and 6-8.

In some embodiments, a subject anti-SIRPα antibody includes an amino acid sequence that is 80% or more, 85% or more, 90% or more, 92% or more, 95% or more, 97% or more, 98% or more, 99% or more, 99.5% or more, or 100% identical to a CDR amino acid sequence set forth in any of SEQ ID NOs: 3-5 and 6-8. In some cases, a subject anti-SIRPα antibody includes a heavy chain having one or more (e.g., two or more, three or more, or 3) of the amino acid sequences set forth in SEQ ID NOs: 3-5. In some cases, a subject anti-SIRPα antibody includes a heavy chain having all 3 of the amino acid sequences set forth in SEQ ID NOs: 3-5. In some cases, a subject anti-SIRPα antibody includes a light chain having one or more (e.g., two or more, three or more, or 3) of the amino acid sequences set forth in SEQ ID NOs: 6-8. In some cases, a subject anti-SIRPα antibody includes a light chain having all 3 of the amino acid sequences set forth in SEQ ID NOs: 6-8.

In some cases, a subject anti-SIRPα antibody includes a light chain having all 3 of the amino acid sequences set forth in SEQ ID NOs: 6-8, and a heavy chain having all 3 of the amino acid sequences set forth in SEQ ID NOs: 3-5.

In some cases, a subject anti-SIRPα antibody includes a heavy chain having three CDRs, where CDR-H1 has the amino acid sequence set forth in SEQ ID NO: 3, CDR-H2 has the amino acid sequence set forth in SEQ ID NO: 4, and CDR-H3 has the amino acid sequence set forth in SEQ ID NO: 5. In some cases, a subject anti-SIRPα antibody includes a light chain having three CDRs, where CDR-L1 has the amino acid sequence set forth in SEQ ID NO: 6, CDR-L2 has the amino acid sequence set forth in SEQ ID NO: 7, and CDR-L3 has the amino acid sequence set forth in SEQ ID NO: 8. In some cases, a subject anti-SIRPα antibody includes: (i) a heavy chain having three CDRs, where CDR-H1 has the amino acid sequence set forth in SEQ ID NO: 3, CDR-H2 has the amino acid sequence set forth in SEQ ID NO: 4, and CDR-H3 has the amino acid sequence set forth in SEQ ID NO:5; and (ii) a light chain having three CDRs, where CDR-L1 has the amino acid sequence set forth in SEQ ID NO: 6, CDR-L2 has the amino acid sequence set forth in SEQ ID NO: 7, and CDR-L3 has the amino acid sequence set forth in SEQ ID NO: 8.

In some embodiments, a subject antibody is a bispecific antibody. The terms "multispecific" or "bispecific" antibodies (also known as bifunctional antibodies or multifunctional antibodies) refer to antibodies that recognize two or more different antigens by virtue of possessing at least one region (e.g., derived from a variable region of a first antibody) that is specific for a first antigen, and at least a second region (e.g., derived from a variable region of a second antibody) that is specific for a second antigen. A bispecific antibody specifically binds to two target antigens and is thus one type of multispecific antibody. Multispecific antibodies can be produced by recombinant DNA methods or include, but are not limited to, antibodies produced chemically by any convenient method. Bispecific antibodies include all antibodies or conjugates of antibodies, or polymeric forms of antibodies which are capable of recognizing two different antigens. Bispecific antibodies include antibodies that have been reduced and reformed so as to retain their bivalent characteristics and to antibodies that have been chemically coupled so that they can have several antigen recognition sites for each antigen.

Subject bispecific antibodies are directed against SIRPα and a second antigen. Subject bispecific antibodies will allow for the phagocytosis of cellular populations expressing the second antigen. Exemplary bispecific antibodies include those targeting a combination of SIRPα and a cancer cell marker, such as, CD19, CD20, CD22, CD24, CD25, CD30, CD33, CD38, CD44, CD52, CD56, CD70, CD96, CD97, CD99, CD123, CD279 (PD-1), CD274 (PD-L1); EGFR, HER2, CD117, C-Met, PTHR2, HAVCR2 (TIM3), etc. As such, in some cases, a subject antibody is a bispecific or multispecific antibody that specifically binds to SIRPα and at least a second antigen. In some such cases, the second antigen is selected from: CD19, CD20, CD22, CD24, CD25, CD30, CD33, CD38, CD44, CD52, CD56, CD70, CD96, CD97, CD99, CD123, CD279 (PD-1), CD274 (PD-L1); EGFR, HER2, CD117, C-Met, PTHR2, HAVCR2 (TIM3).

In some cases, an exemplary bispecific antibody includes a sequence (e.g., CDRs) disclosed herein that provides specific binding to SIRPα as well as sequences (e.g., CDRs) from antibodies that bind a cancer cell marker. Examples of antibodies with CDRs that provide specific binding to a cancer cell marker include, but are not limited to: CETUXIMAB (binds EGFR), PANITUMUMAB (binds EGFR), RITUXIMAB (binds CD20), TRASTUZUMAB (binds HER2), PERTUZUMAB (binds HER2), ALEMTUZUMAB (binds CD52), BRENTUXIMAB (binds CD30), and the like.

Methods to generate bispecific antibodies are described in the literature, for example, in U.S. Pat. Nos. 5,989,830, 5,798,229, which are incorporated herein by reference. Higher order specificities, e.g. trispecific antibodies, are described by Holliger and Hudson (2005) Nature Biotechnology 23:1126-1136.

Within the context of the present disclosure, antibodies are understood to include monoclonal antibodies and polyclonal antibodies, antibody fragments (e.g., Fab and F(ab')$_2$), chimeric antibodies bifunctional or bispecific antibodies and tetrameric antibody complexes. Antibodies may also be described or specified in terms of their binding affinities of the variable region for an epitope, i.e. for SIRPα, including those characterized by a $K_d$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). For bispecific and/or multispecific antibodies, which have more than one specificity (i.e., more than 1 binding constant), each antigen-specific region can have a $K_d$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less).

Antibodies may be characterized by reduced binding to one or more FcR other than FcRn, where the binding to one or more FcR, including without limitation or more FcγR is reduced by at least about 10%, at least about 20%, at least about 30%, at least about 40%, at least about 50%, at least about 60%, at least about 70%, at least about 80%, at least about 90%, at least about 95%, at least about 99%, or more.

Nucleic Acids

The disclosure also provides isolated nucleic acids encoding subject anti-SIRPα antibodies (e.g., including any of the polypeptides discussed above), vectors and host cells comprising the nucleic acid, and recombinant techniques for the production of the antibody. As is known in the art, a variable region sequence may be fused to any appropriate constant region sequence.

For recombinant production of the antibody, the nucleic acid encoding can be inserted into a replicable vector for further cloning (amplification of the DNA) or for expression. DNA encoding a subject antibody can be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

A subject anti-SIRPα antibody of this disclosure may be produced recombinantly not only directly, but also as a fusion polypeptide with a heterologous or homologous polypeptide, which include a signal sequence or other polypeptide having a specific cleavage site at the N-terminus of the mature protein or polypeptide, an immunoglobulin constant region sequence, and the like. A heterologous signal sequence selected preferably may be one that is recognized and processed (i.e., cleaved by a signal peptidase) by the host cell. For prokaryotic host cells that do not recognize and process the native antibody signal sequence, the signal sequence is substituted by a prokaryotic signal sequence selected.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

Examples of suitable host cells for cloning or expressing subject nucleic acids include, but are not necessary limited to prokaryote, yeast, or higher eukaryote cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1.982)); MRC 5 cells; FS4 cells; and a human hepatoma line (Hep G2). Host cells are transformed with the above-described expression or cloning vectors for anti-SIRPα antibody production and cultured in conventional nutrient media modified as appropriate for inducing promoters, selecting transformants, or amplifying the genes encoding the desired sequences.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is usually recommended for human IgG3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $CH_3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Methods of Use

The anti-SIRPα antibodies provided herein can be used in the modulation of phagocytosis (e.g. inducing phagocytosis), particularly for in vivo therapeutic uses. For example, the subject anti-SIRPα antibodies provided herein can be used, in any method where the interaction between CD47 on one cell and SIRPα on another is to be blocked. Exemplary methods for using a subject anti-SIRPα antibody include, but are not limited to those methods described in U.S. patent applications: 20130142786, 20120282174, 20110076683, 20120225073, 20110076683, 20110015090, 20110014119, 20100239579, 20090191202, 20070238127, 20070111238, and 20040018531; which are hereby specifically incorporated by reference in their entirety. For example, antibody compositions may be administered to induce phagocytosis of cancer cells, inflammatory cells, and/or chronically infected cells that express CD47.

A subject anti-SIRPα antibody provided herein may administered, alone or in combination with another antibody to a subject to treat symptoms, illnesses, and/or diseases. Examples of symptoms, illnesses, and/or diseases that can be treated with a subject anti-SIRPα antibody include, but are not limited to cancer (any form of cancer, including but not limited to: carcinomas, soft tissue tumors, sarcomas, teratomas, melanomas, leukemias, lymphomas, brain cancers, solid tumors, mesothelioma (MSTO), etc.); infection (e.g., chronic infection); cardiovascular conditions, e.g. atherosclerosis, aneurysm, etc., and immunological diseases or disorders (e.g., an inflammatory disease)(e.g., multiple sclerosis, arthritis, and the like)(e.g., for immunosuppressive therapy). A subject anti-SIRPα antibody can also be used for transplant conditioning (e.g., stem cell transplant, bone marrow transplant, etc.) (e.g., to destroy malignant cells, to provide immunosuppression to prevent the patient's body from rejecting the donor's cells/stem cells, etc.)

In some embodiments, a subject anti-SIRPα antibody (including, for example, a bispecific macrophage engaging antibody) is used in combination with another antibody to treat an individual. In one embodiment, a subject anti-SIRPα antibody can be combined (co-administered) with monoclonal antibodies directed against one or more cancer markers (e.g., CD19, CD20, CD22, CD24, CD25, CD30, CD33, CD38, CD44, CD52, CD56, CD70, CD96, CD97, CD99, CD123, CD279 (PD-1), CD274 (PD-L1); EGFR, HER2, CD117, C-Met, PTHR2, HAVCR2 (TIM3), and the like). In some cases, the combination compositions can be synergistic in enhancing phagocytosis of target cells as compared to the use of single antibodies. As proof of principle, CD47-directed agents (e.g., anti-CD47 antibodies) exhibit profound anti-tumor synergy with monoclonal antibodies (mAbs) against tumor-specific antigens, such as rituximab (anti-CD20) for B-cell lymphoma and trastuzumab (anti-HER2) for HER2+ breast cancer. The Fc fragments of these mAbs activate Fc receptors (FcRs) on macrophages to drive a phosphorylation cascade propagated by the receptors' ITAMs (Immunoreceptor Tyrosine-based Activation Motifs). As SIRPα signals through counter-opposing ITIMs (Immunoreceptor Tyrosine-based Inhibitory Motifs), blocking SIRPα tips the balance in favor of ITAM signaling, thereby potentiating phagocytosis.

In some embodiments, a subject anti-SIRPα antibody is co-administered with (i.e., administered in combination with) an antibody that specifically binds a second antigen, e.g., a marker of a CD47-expressing cell (e.g., a cancer cell marker, a marker of an infected cell, etc.), including without limitation tumor associated and tumor specific antigens. For example, in some cases, a subject anti-SIRPα antibody is co-administered with 1 or more antibodies selected from: CETUXIMAB (binds EGFR), PANITUMUMAB (binds EGFR), RITUXIMAB (binds CD20), TRASTUZUMAB (binds HER2), PERTUZUMAB (binds HER2), ALEMTUZUMAB (binds CD52), and BRENTUXIMAB (binds CD30) , GEMTUZUMAB (binds CD33), LORVOTUZUMAB (binds CD56), IPILIMUMAB (binds CTLA-4 (CD152)), NIVOLUMAB (binds PD-1 (CD279), AVELUMAB (binds PDL-1), etc.

Therapeutic formulations comprising one or more antibodies of the disclosure are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent the CD47 associated disease.

The therapeutic dose may be at least 0.01 mg/kg body weight, at least 0.05 mg/kg body weight; at least 0.1 mg/kg body weight, at least 0.5 mg/kg body weight, at least 1 mg/kg body weight, at least 2.5 mg/kg body weight, at least 5 mg/kg body weight, at least about 7.5 mg/kg body weight, at least about 10 mg/kg body weight, at least about 15 mg/kg body weight, and not more than 300 mg/kg body weight, not more than about 200 mg/kg body weight, not more than about 100 mg/kg body weight. It will be understood by one of skill in the art that such guidelines will be adjusted for the molecular weight of the active agent, e.g. in the use of antibody fragments, or in the use of antibody conjugates. The dosage may also be varied for localized administration, e.g. intranasal, inhalation, etc., or for systemic administration, e.g. i.m., i.p., i.v., and the like.

The antibody need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The anti-SIRPα antibody is administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the anti-SIRPα antibody is suitably administered by pulse infusion, particularly with declining doses of the antibody.

For the prevention or treatment of disease, the appropriate dosage of antibody will depend on the type of disease to be treated, as defined above, the severity and course of the disease, whether the antibody is administered for preventive purposes, previous therapy, the patient's clinical history and response to the antibody, and the discretion of the attending physician. The antibody is suitably administered to the patient at one time or over a series of treatments.

In another embodiment of the disclosure, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). An active agent in the composition can be the anti-SIRPα antibody. The label on, or associated with, the container can indicate that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

A subject anti-SIRPα antibody of the present disclosure can be provided in a kit, i.e., a packaged combination of reagents in predetermined amounts with instructions for administration and/or for performing an assay. In some cases, a subject kit can include one or more additional antibodies that can be used in combination with an anti-SIRPα antibody. For example, in some cases, a subject kit includes one or more antibodies that each binds a second antigen (e.g., a cancer cell marker). In some embodiments, the second antigen is an antigen selected from: CD19, CD20, CD22, CD24, CD25, CD30, CD33, CD38, CD44, CD52, CD56, CD70, CD96, CD97, CD99, CD123, CD279 (PD-1), CD274 (PD-L1); EGFR, HER2, CD117, C-Met, PTHR2, and HAVCR2 (TIM3). In some embodiments, a subject kit includes a subject SIRPα antibody and one or more antibodies selected from: CETUXIMAB (binds EGFR), PANITUMUMAB (binds EGFR), RITUXIMAB (binds CD20), TRASTUZUMAB (binds HER2), PERTUZUMAB (binds HER2), ALEMTUZUMAB (binds CD52), and BRENTUXIMAB (binds CD30), GEMTUZUMAB (binds CD33), LORVOTUZUMAB (binds CD56), IPILIMUMAB (binds CTLA-4 (CD152)), and NIVOLUMAB (binds PD-1 (CD279)).

When the antibody is labeled with an enzyme, the kit can include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Blocking the CD47-SIRPα pathway mediates phagocytosis of cancer cells and synergizes with cancer-targeting monoclonal antibodies. Blocking agents include, for example, antibodies that specifically bind to CD47, and antibodies that specifically bind to SIRPα. The latter may have certain advantages in therapeutic applications because expression of SIRPα is more restricted than CD47. This may impact pharmacokinetics and the toxicology profile.

Following administration to a patient, a desirable agent will retain biological activity for a period of time sufficient to effect a therapeutic benefit. For example, in the treatment of cancer and other chronic conditions, a half like of days to weeks may be preferred. Antibodies comprising an Fc region can readily achieve this level of stability, which is thought to be mediated, at least in part, by interaction of the Fc region with the low affinity receptor, hFcRn, which is involved in recycling and transport of IgG.

Another desirable attribute of therapeutic agents is minimal immunogenicity when administered to a patient. For this reason, antibodies for human therapy are typically modified to comprise at least a human Fc region (in the case of chimeric antibodies); or human framework and constant regions (in the case of humanized antibodies). The therapeutic use of antibodies that have a xenogeneic Fc region is generally counter-indicated.

It is important to note that for various purposes, in vitro model systems, or engineered in vivo animal models, may be used to determine the toxicity and efficacy of an agent. In such model systems, there may be a "mismatch" of the target cells and the effector cells that are present, e.g. where human cancer cells are xenografted into a mouse. While useful for many purposes, such models may not accurately predict the activity of activity of an antibody in a patient setting, where the target cells and the effector cells will be of the same species, e.g. human. For these reasons, advantageous information about therapeutic efficacy is obtained by testing the activity of a human or humanized antibody against human target cells, in the presence of human effector cells.

Native human antibodies are glycoproteins that contain a ubiquitous N-linked glycan at position N297 of the Fc domain (Eu numbering). Studies have demonstrated that altering glycosylation at N297 can modify interactions with FcγRs and thereby affect antibody effector functions. The absence of the glycan at N297 abolishes binding to FcγRs and antibody effector functions. Other amino acid changes in Fc regions include the double substitution, L234A/L235A (LALA), which greatly reduces binding to FcγRs. Aglycosylated antibodies produced in E. coli also have minimal binding to FcγRs and can provide a simplified and more economical antibody production platform.

In preparing anti-SIRPα antibodies for therapeutic purposes, the KWAR23 antibody (disclosed in International Application WO 2015/138600, herein specifically incorporated by reference) was modified to comprise a human Fc region. Surprisingly it was found that the change in Fc region was detrimental to activity in enhancing phagocytosis when combined with cancer targeting monoclonal antibodies in a human effector cell setting.

It was hypothesized that simultaneous engagement of SIRPα and high affinity Fcγ receptors present on effector cells resulted in inhibition of phagocytosis, e.g. through formation of a trimolecular complex between the antibody, Fcγ receptor, and SIRPα on the cell surface. To address the issue, Fcγ receptor engagement was blocked by replacing the Fc of the anti-SIRPα antibody with a so-called "dead Fc", i.e. an Fc region engineered to have reduced binding to Fcγ receptors by the introduction of amino acid changes. The specific engineered Fc region comprised an N297A amino acid substitution in the human IgG1 constant region. As shown in FIG. 1, this modification did overcome the inhibitory effect and restored the desired phagocytosis promoting effect.

Example 2

Anti-SIRPα antibodies with reduced FcγR binding for phagocytosis of NHL cells by human macrophages in combination with rituximab in vitro. Anti-human SIRPα antibodies comprising an engineered Fc region, as discussed in Example 1, are assessed for the ability to enable phagocytosis of human NHL cell lines, primary NHL cells, and normal peripheral blood (NPB) cells by human macrophages in vitro. NHL cells are incubated in the presence of IgG1 isotype control or anti-CD45 IgG1 antibody, and compared to the activity in the presence of a humanized anti-SIRPα antibody with a wild-type or engineered N297A Fc region, in the presence of rituximab. The phagocytosis of the tumor cells under these conditions is measured.

Cell Lines. A Burkitt's lymphoma cell line (Raji) and a DLBCL cell line (SUDHL4) are obtained from the American Type Culture Collection or generated in the lab. The NHL17* cell line is generated from a patient with DLBCL by culturing bulk cells in vitro with IMDM supplemented with 10% human AB serum for 1.5 months.

Human Samples. Normal human peripheral blood and human NHL samples are obtained with informed consent, according to an IRB-approved protocol or with informed consent from the Norwegian Radium Hospital (Oslo, Norway) according to a Regional Ethic Committee (REK)-approved protocol. Normal tonsils for germinal center B cell analysis are obtained from discarded tonsillectomy specimens from consented pediatric patients.

Flow Cytometry Analysis. For analysis of normal peripheral blood cells, germinal center B cells, and primary NHL cells, the following antibodies were used: CD19, CD20, CD3, CD10, CD45, CD5, CD38 (Invitrogen, Carlsbad, Calif., USA and BD Biosciences, San Jose, Calif., USA). Analysis of CD47 expression is performed with an antihuman CD47 FITC antibody (clone B6H12.2, BD Biosciences). Cell staining and flow cytometry analysis was performed as previously described.

Therapeutic Antibodies. Rituximab (anti-CD20, human IgG1) is obtained from the Stanford University Medical Center, mouse anti-human CD20, IgG2a from Beckman Coulter (Miami, Fla., USA).

In Vitro Isobologram Studies. In vitro phagocytosis assays are conducted with NHL cells incubated with the indicated antibodies, anti-CD20 IgG2a, or rituximab either alone or in combination at concentrations from 1 µg/ml to 10 µg/ml. The concentration of each antibody required to produce a defined single-agent effect (phagocytic index) is determined for each cell type. Concentrations of the two antibodies combined to achieve this same phagocytic index were then plotted on an isobologram and the combination index (CI) determined. The CI is calculated from the formula CI=(d1/D1)+(d2/D2), whereby d1=dose of drug 1 in combination to achieve the phagocytic index, d2=dose of drug 2 in combination to achieve the phagocytic index, D1=dose of drug 1 alone to achieve the phagocytic index, D2=dose of drug 2 alone to achieve the phagocytic index. A CI of less than, equal to, and greater than 1 indicates synergy, additivity, and antagonism, respectively.

Example 3

Anti-SIRPα antibodies with reduced FcγR binding for phagocytosis of colorectal cancer cells by human macrophages in combination with anti-EGFR in vitro. Cancer Cells. DLD1 cells (ATCC), HT29 cells (ATCC), SW620 cells (ATCC), SW48 cells (ATCC), LS174T cells (ATCC), HCT116 cells (ATCC), and CACO-2 cells (ATCC) are cultured in RPMI (ThermoFisher S.) (DLD1), EMEM (ThermoFisher S.) (CACO-2, LS174T), McCoy's 5A (ThermoFisher S.) (HT29, HCT116), or Leibovitz's L-15 (ThermoFisher S.) (SW48, SW 620) supplemented with 10% fetal bovine serum (Omega Scientific), 100 U/mL penicillin and 100 µg/mL streptomycin (ThermoFisher S). GFP-luciferase+DLD1 cell line was generated by transduction using a pCDH-CMV-MCS-EF1 puro HIV-based lentiviral vector (Systems Biosciences) engineered to express an eGFP-luciferase2 (pgl4) fusion protein. Stable lines were created by sorting for GFP expression on FACSAria II cell sorters (BD Biosciences). Tumor cells were transduced overnight with lentivirus in culture media containing 6 µg/mL polybrene. The following day, cells were washed repeatedly to remove polybrene and extracellular lentivirus. Transduced (GFP+) cells were later isolated from xenograft tumors by FACS.

In Vitro Phagocytosis Assay. Peripheral blood mononuclear cells are enriched by density gradient centrifugation and monocytes purified with anti-CD14 microbeads (Miltenyi) and differentiated to macrophages by culture for 7-10 days in IMDM+GlutaMax (Invitrogen) supplemented with 10% AB-Human Serum (Invitrogen) and 100 U/mL penicillin and 100 µg/mL streptomycin (Invitrogen). Phagocytosis assays are performed by co-culture of 50,000 macrophages with 100,000 GFP+ tumor cells for 2 hours, then analyzed using an LSRFortessa cell analyzer with high throughput sampler (BD Biosciences). Antibodies used for treatment include: IgG1 isotype control, anti-SIRPα with an active or dead Fc region, and anti-EGFR cetuximab (Bristoll-Myers Squibb). Macrophages are identified by flow cytometry using anti-CD206 antibody. Dead cells were excluded from the analysis by staining with DAPI (Sigma). Phagocytosis is evaluated as the percentage of GFP+ macrophages and normalized to the maximal response by each independent donor against each cell line.

Example 4

Avelumab in Combination With Anti-SIRPα in Advanced Malignancies

Using the assays described above, the combination of anti-SIRPα antibody with a wild-type or dead Fc is tested for phagocytosis and/or cell mediated cytolysis in vitro of advanced or metastatic solid tumors [eg, non-small cell lung cancer (NSCLC), melanoma, and squamous cell carcinoma of the head and neck (SCCHN)] in combination with avelumab (MSB0010718C), an anti-PD-L1 antibody.

Example 5

Variability in Individual Responses

Antibodies were generated with anti-SIRPα KWAR23 variable region with a mouse Fc sequence (designated mKWAR); a chimeric with a human Fc sequence comprising N297A mutation to abrogate interaction with human FcγRs (designated chKWAR-dead-Fc); a chimeric with a wild-type human IgG1 Fc (designated chKWAR-IgG1); and a chimeric with human IgG4 Fc region, (designated chKWAR-IgG4).

Figure 2:
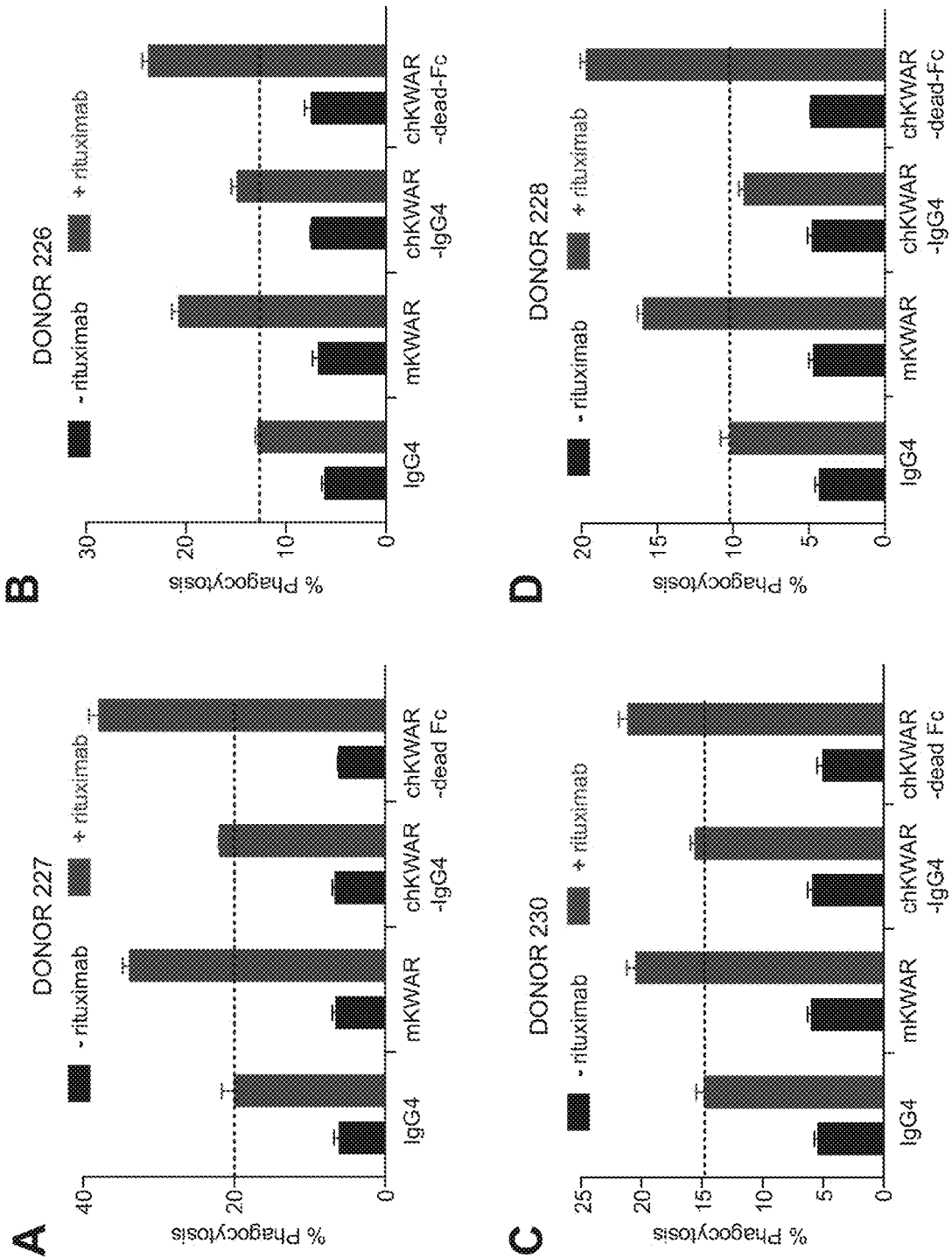
FIG. 2, panels A-J. Determining synergy of variants of the anti-SIRPalpha antibody KWAR with rituximab to promote macrophage-mediated phagocytosis of Raji lymphoma cells.
Figure 2:
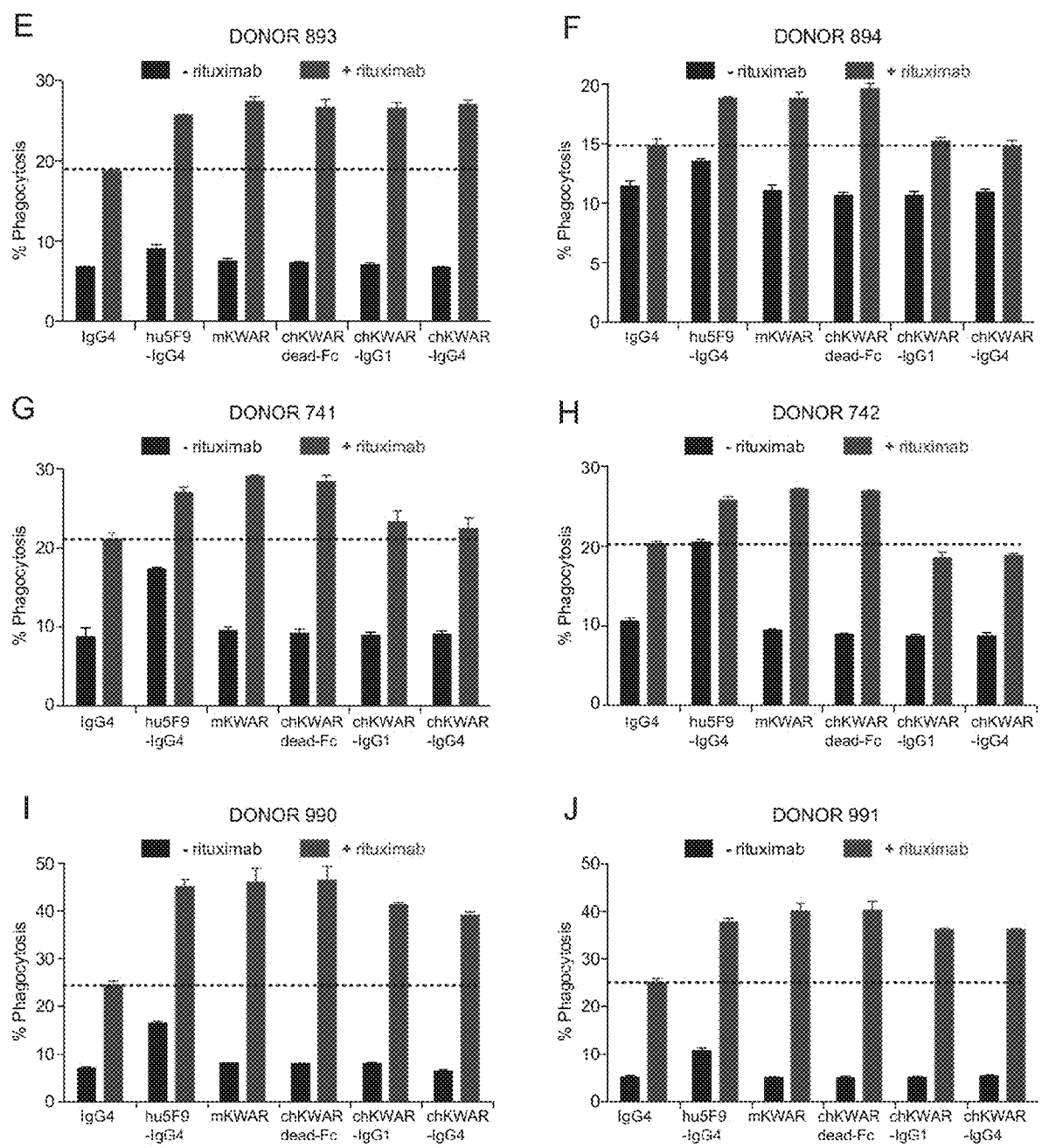

The antibodies were assayed for a synergistic response in enhancing phagocytosis of cancer cells, when combined with rituximab, data shown in FIG. 2.

Human macrophages from 10 different donors were differentiated from monocytes, as indicated by DONOR #, in the presence of human serum for 7 days. Raji lymphoma cells were labeled with CFSE (Carboxyfluorescein succinimidyl ester is a fluorescent cell staining dye) and incubated with the macrophages in the presence of 10 µg/ml rituximab (anti-CD20 Ab) alone, in combination with 10 µg/ml of the KWAR variants or human IgG4 as control. After two-hour incubation, phagocytosis was determined by flow cytometry analysis as CFSE-positive macrophages. Baseline phagocytosis was determined with the human IgG4 control Ab. Combination of rituximab with human IgG control Ab was used to establish rituximab specific baseline phagocytosis The dotted line indicates the level of phagocytosis with rituximab alone.

In testing responses from multiple individuals, it was found that there was inter-individual variability in the enhancement of phagocytosis. The combination of rituximab with murine anti-SIRPα Ab (mKWAR) enhanced phagocytosis for all ten donor macrophages compared to rituximab alone (indicated as increase above dotted line).

In contrast, the combination of rituximab with chimeric anti-SIRPα Ab (chKWAR-IgG4) showed a significant enhancement of phagocytosis for donor macrophages for three donors, but not for the other seven donors. Similarly, in the 6 donors tested with a wild-type IgG1 Fc region (chKWAR-IgG1) half of the donors showed no significant enhancement over control.

In contrast, all ten donors had a significant enhancement of phagocytosis when the chimeric anti-SIRPα Ab with a "dead" IgG1-Fc region (KWAR-dead-Fc) was combined with rituximab.

These experiments demonstrate the general benefit of the dead-Fc construct for anti-SIRPα antibodies, in reducing variability of responsiveness, i.e. reducing the number of individuals that are non-responders in the enhancement of phagocytosis when combined with a cell-targeted antibody.

Example 6

Additional Anti-SIRPα Antibodies

Additional antibodies were raised to human SIRPα by immunizing mice with the human protein, and screening for antibodies that bound to the SIRPα. Two monoclonal antibody clones were designated 9B11 and 7E11, respectively. The mouse variable regions were joined as a chimera to human IgG4 Fc region (designated as 7E11-G4 or 9B11-G4), or to a human IgG1 Fc region comprising N297A mutation to abrogate interaction with human FcγRs (designated as 7E11-G1 or 9B11-G1).

Figure 3:
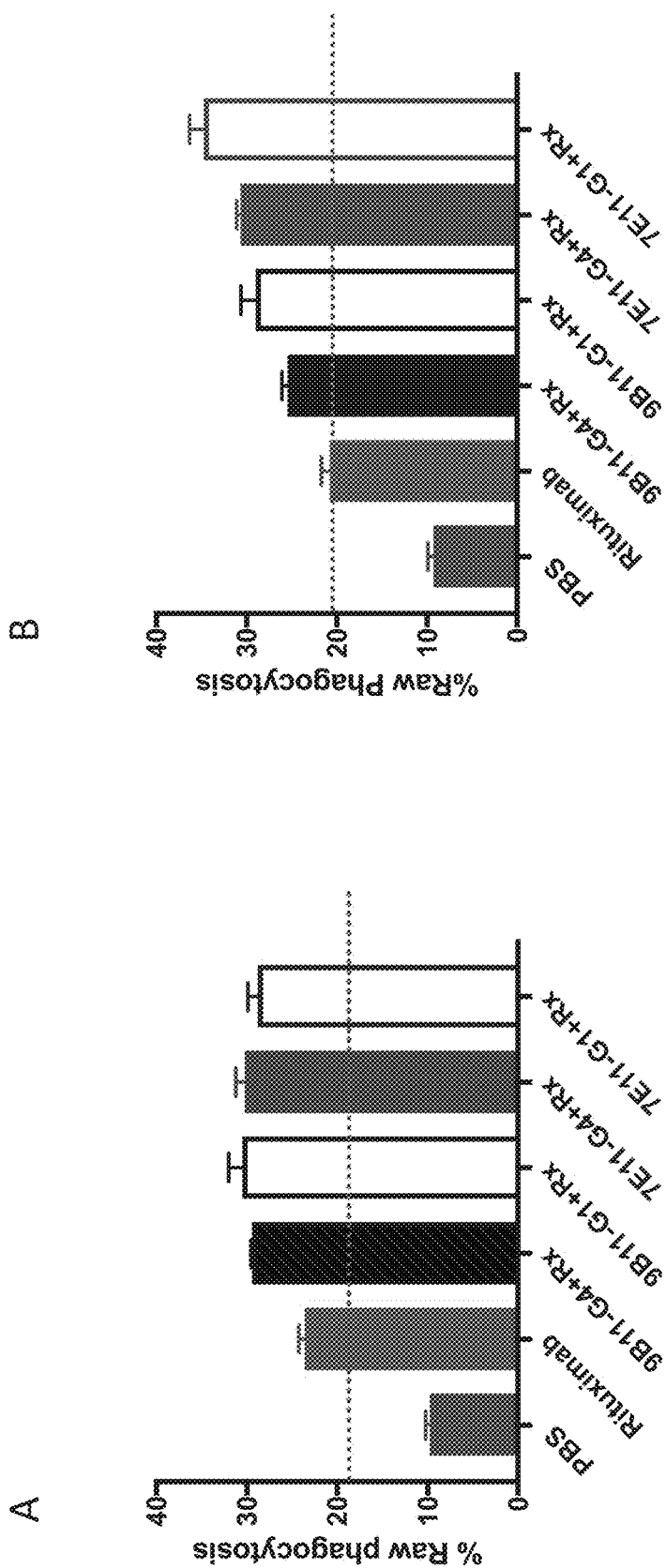
FIG. 3, panels A-B. 9B11 and 7E11 synergize with rituximab to promote macrophage-mediated phagocytosis of Raji cells.

As was found with KWAR23, the 9B11 and 7E11 antibodies showed a synergistic response in enhancing phagocytosis of cancer cells when combined with Rituximab. Shown in FIG. 3, macrophages were differentiated from monocytes of donor A (A) and donor B (B) in the presence of human serum for 7 days. Raji cells were labeled with CFSE and incubated with the macrophages in the presence of 10 μg/ml rituximab (Rx) alone or in combination with 10 μg/ml of 9B11-G4, 9B11-G1, 7E11-G4, or 7E11-G1. Two hours later, Phagocytosis percentage was calculated by Flow Cytometry analysis looking for GFP+ Macrophages.

The data show that while both the IgG4 formatted antibodies and mutated IgG1 formatted antibodies could provide for a synergistic response, but the mutated IgG1 format provided a more consistent response across donors.

Example 7

F(ab)2 Fragments

As an alternative to the use of an antibody comprising a human Fc region with reduced affinity for an Fcγ receptor, an antibody can be engineered to lack Fc sequences, e.g. by producing an F(ab')2 fragment.

The anti-SIRPα antibody KWAR23, disclosed, for example in US patent application US-2017-0073414-A1, herein specifically incorporated by reference was originally developed as a mouse anti-human antibody. To generate an F(ab)2 fragment, the purified antibody is suspended with Pierce F(ab')2 Preparation pepsin immobilized on settled resin, according to the manufacturer's instructions. Pepsin digestion typically produces a F(ab')2 fragment (~110 kDa by SDS-PAGE under non-reducing conditions) and numerous small peptides of the Fc portion. The resulting F(ab')2 fragment is composed of a pair of Fab' units connected by two disulfide bonds. The Fc fragment is extensively degraded and separated from F(ab')2 by dialysis, gel filtration or ion exchange chromatography.

Example 8

Humanized KWAR Antibody

The anti-SIRPα antibody KWAR23, disclosed, for example in US patent application US-2017-0073414-A1, herein specifically incorporated by reference was originally developed as a mouse anti-human antibody.

Mouse KWAR23 variable heavy chain (VH) (CDRs are underlined)

```
                                        (SEQ ID NO: 9)
EVQLQQSGAELVKPGASVKLSCTASGFNIKDYYIHWVQQRTEQGLEWIGR

IDPEDGETKYAPKFQDKATITADTSSNTAYLHLSSLTSEDTAVYYCARWG

AYWGQGTLVTVSS
```

Mouse KWAR23 variable light chain (VL) (CDRs are underlined)

```
                                       (SEQ ID NO: 10)
QIVLTQSPAIMSASPGEKVTLTCSASSSVSSSYLYWYQQKPGSSPKLWIY

STSNLASGVPARFSGSGSGTSYSLTISSMEAEDAASYFCHQWSSYPRTFG

AGTKLELK
```

Humanized KWAR23 variable heavy chain (VH), SEQ ID NO:1:

```
EVQLVQSGAEVKKPGATVKISCKVSGFNIKDYYIHWVQQAPGKGLEWIGR

IDPEDGETKYAPKFQDRATITADTSTDTAYMELSSLRSEDTAVYYCARWG

AYWGQGTLVTVSS
```

Humanized KWAR23 variable light chain (VL), SEQ ID NO:2:

```
QIVLTQSPPTLSLSPGERVTLTCSASSSVSSSYLYWYQQKPGQAPKLWIY

STSNLASGVPARFSGSGSGTSYTLTISSLQPEDFAVYFCHQWSSYPRTFG

AGTKLEIK
```

The CDRs of KWAR23 variable heavy chain (defined by IMGT) are as follows:

```
CDR-H1:
                                        (SEQ ID NO: 3)
DYYIH

CDR-H2:
                                        (SEQ ID NO: 4)
RIDPEDGETKYAPKFQD

CDR-H3:
                                        (SEQ ID NO: 5)
WGAY
```

The CDRs of KWAR23 variable light chain (defined by IMGT) are as follows:

CDR-L1:
(SEQ ID NO: 6)
SASSSVSSSYLY

CDR-L2:
(SEQ ID NO: 7)
STSNLAS

CDR-L3:
(SEQ ID NO: 8)
HQWSSYPRT

In order to select human antibody frameworks (FR) to be used as templates for CDR-grafting, mouse KWAR23 VL and VH regions were compared with those of human germline sequences. Human framework sequences were selected based on the mouse framework sequences. The FRs from human selected sequences provided the starting point for designing humanized KWAR23. Residues in the FRs identical to the mouse sequences were retained and non-identical residues were either retained or substituted based on molecular modeling. The humanized KWAR23 coding sequences were transfected into cells, and purified. The sequences are shown in FIG. 4.

Next, the ability of humanized KWAR23 to recognize human SIRPα was examined by Biacore assay. The binding affinity of the mouse antibody was determined to be $1.18 \times 10^{-9}$ M. The binding affinity of the humanized antibody was determined to be $1.54 \times 10^{-9}$ M.

Figure 5:
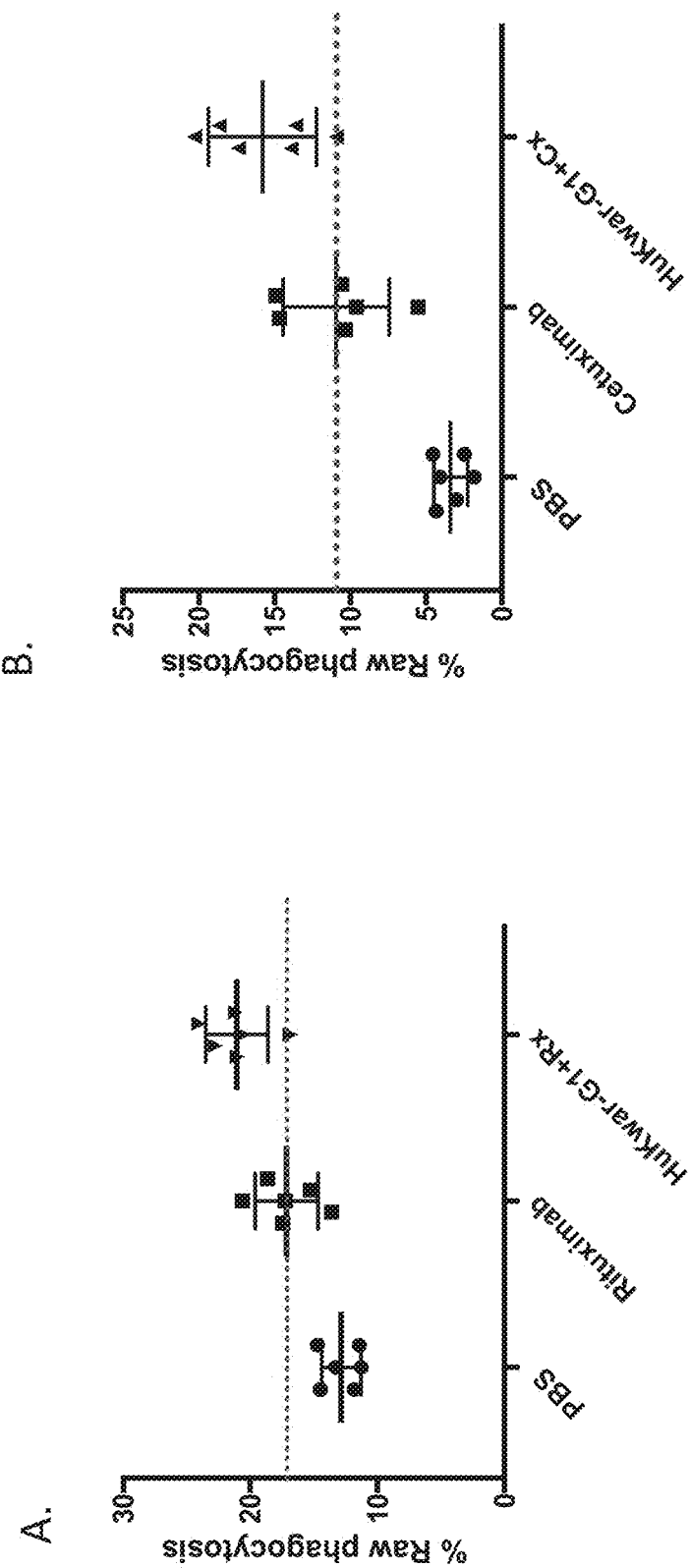
FIG. 5, panels A-B. Humanized Kwar synergizes with therapeutic antibodies to promote phagocytosis.

Humanized Kwar was tested for synergy with therapeutic antibodies to promote phagocytosis, shown in FIG. 5. (A) Raji cells were labeled with CFSE and incubated with human monocyte derived macrophages in the presence of 10 µg/ml rituximab alone or in combination with 10 µg/ml of HuKwar-G1. Data presented was results from 6 individual donors. (B) HT29 cells were labeled with CFSE and incubated with human monocyte derived macrophages in the presence of 0.1 ug/ml cetuximab alone or in combination with 10 ug/ml of HuKwar-G1. Two hours later, Phagocytosis percentage was calculated by Flow Cytometry analysis looking for GFP+ Macrophages. Data presented was results from 6 individual donors. Human IgG1 is engineered to have a N297A mutation to abrogate the interaction with human FcγRs. The data show a synergy of response for the humanized antibody with both tumor-specific antibodies.

In summary, we have developed therapeutic antibodies based on the mouse monoclonal antibody KWAR23 directed against human SIRPα, by using methods to create a mouse/human chimeric antibody and a humanized antibody. The chimeric and humanized antibodies retain the ability to specifically bind SIRPα.

That which is claimed is:

1. An isolated, therapeutic antibody comprising:
   (i) a variable region that specifically binds to human SIRPα, comprising a light chain having all three of amino acid sequences set forth in SEQ ID NOs: 6-8, and a heavy chain having all three amino acid sequences set forth in SEQ ID NOs: 3-5;
   (ii) a human Fc region comprising an amino acid substitution (a) in the CH2 region at EU index positions 234, 235, or 237; or (b) at EU index position asparagine 297, which amino acid substitution reduces binding to a human Fcγ receptor, relative to a wild-type Fc region.

2. The antibody of claim 1, comprising an amino acid substitution of N297A/Q/D/H/G/C.

3. The antibody of claim 1, wherein the amino acid substitution is L234A/L235A.

4. The antibody of claim 2, further comprising the amino acid substitution K322A.

5. The antibody of claim 1, wherein the amino acid substitution comprises E233P/L234V/L235A/G236+A327G/A330S/P331S.

6. The antibody of claim 1, comprising the variable region sequences of SEQ ID NO:1 and SEQ ID NO:2; or SEQ ID NO:9 and SEQ ID NO:10.

7. A pharmaceutical composition comprising an antibody set forth in claim 1.

8. The composition of claim 7, in a unit dose formulation.

9. The composition of claim 8, provided as a sterile pre-pack in a unit dose with diluent.

10. The composition of claim 7, further comprising a second therapeutic antibody.

11. A method of increasing phagocytosis of a targeted cell in a human subject, the method comprising:
    administering to the subject a composition comprising an antibody set forth in claim 1, in a dose effective to increase phagocytosis of the targeted cell.

12. The method according to claim 11, wherein the targeted cell is a cancer cell.

13. The method according to claim 11, further comprising administering a second therapeutic antibody.

14. The method of claim 13, wherein the second therapeutic antibody binds to a protein on the surface of a cancer cell.

* * * * *